US011553978B2

(12) United States Patent
Ago et al.

(10) Patent No.: US 11,553,978 B2
(45) Date of Patent: Jan. 17, 2023

(54) STOPPER AND ADAPTOR

(71) Applicant: MEDICAROID CORPORATION, Kobe (JP)

(72) Inventors: Kenji Ago, Kobe (JP); Kaoru Takahashi, Kobe (JP); Yu Usuki, Kobe (JP); Shota Betsugi, Kobe (JP); Tomoaki Noda, Kobe (JP); Yoshiaki Tanaka, Kobe (JP); Tetsuya Nakanishi, Kobe (JP); Kazuhiro Sato, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 456 days.

(21) Appl. No.: 16/828,956

(22) Filed: Mar. 25, 2020

(65) Prior Publication Data

US 2020/0305997 A1 Oct. 1, 2020

(30) Foreign Application Priority Data

Mar. 28, 2019 (JP) .............................. JP2019-062801
Oct. 25, 2019 (JP) .............................. JP2019-194785

(51) Int. Cl.
 *B25J 5/00* (2006.01)
 *A61B 90/00* (2016.01)
 *A61B 34/37* (2016.01)
 *A61B 34/00* (2016.01)
 *A61B 34/30* (2016.01)

(52) U.S. Cl.
 CPC .............. *A61B 90/03* (2016.02); *A61B 34/37* (2016.02); *A61B 34/71* (2016.02); *A61B 2034/301* (2016.02); *A61B 2090/035* (2016.02)

(58) Field of Classification Search
 CPC .......................... A61B 90/03; A61B 2090/035
 See application file for complete search history.

(56) References Cited

U.S. PATENT DOCUMENTS

| 9,050,125 | B2 | 6/2015 | Boudreaux et al. |
|---|---|---|---|
| 2006/0161138 | A1 | 7/2006 | Orban, III et al. |
| 2010/0174293 | A1 | 7/2010 | Orban, III et al. |
| 2012/0247489 | A1 | 10/2012 | Orban, III et al. |
| 2016/0361131 | A1 | 12/2016 | Dachs, II et al. |
| 2019/0365494 | A1 | 12/2019 | Dachs, II et al. |
| 2022/0117691 | A1* | 4/2022 | Ago ........................ A61B 34/37 |

FOREIGN PATENT DOCUMENTS

| JP | 2006-156138 A | 6/2006 |
|---|---|---|
| JP | 5403864 B2 | 1/2014 |
| JP | 2017-512557 A | 5/2017 |
| WO | 2016/176170 A1 | 11/2016 |

\* cited by examiner

*Primary Examiner* — Karen Masih
(74) *Attorney, Agent, or Firm* — Metrolex IP Law Group, PLLC

(57) ABSTRACT

A stopper according to one or more embodiments may include: a stopper body; and a rotation restriction portion provided at the stopper body and configured to restrict rotations of the drive transmission member. The stopper may be configured such that the rotation restriction portion restricts the rotations of the drive transmission member in a state where the stopper body is attached to the adaptor main body and the rotation restriction portion releases the restriction of the rotations of the drive transmission member in a state where the stopper body is detached from the adaptor main body.

20 Claims, 27 Drawing Sheets

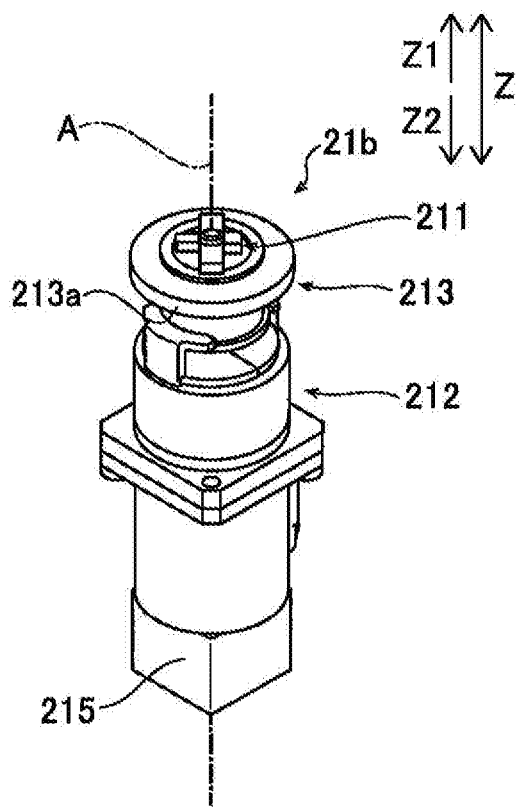
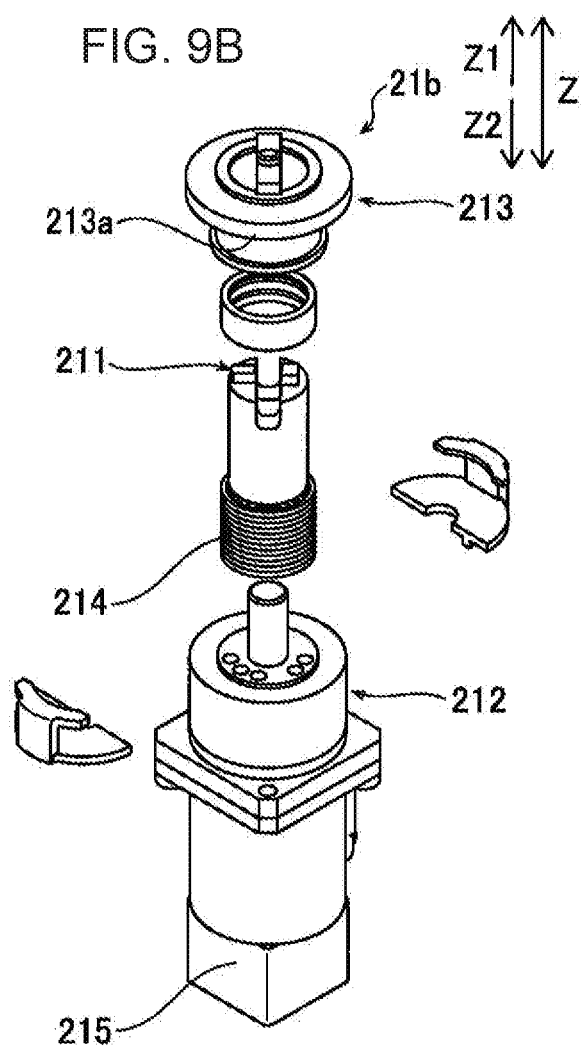

SURGICAL INSTRUMENT IS MOUNTED BUT NOT ENGAGED

SURGICAL INSTRUMENT IS MOUNTED AND ENGAGED

CROSS SECTION ALONG LINE 101-101

SECOND EMBODIMENT

CROSS SECTION ALONG LINE 8000-8000

CROSS SECTION ALONG LINE 8001-8001

STOPPER AND ADAPTOR

CROSS-REFERENCE TO RELATED APPLICATIONS

This application claims priority to Japanese Patent Application No. 2019-062801 filed on Mar. 28, 2019 and Japanese Patent Application No. 2019-194785 filed on Oct. 25, 2019, the entire contents of which are incorporated herein by reference.

BACKGROUND

The disclosure may relate to a stopper and an adaptor, and more particularly to a stopper including a rotation restriction portion that restricts rotations of a drive transmission member and to an adaptor including the stopper.

In a related art, an adaptor including a rotation restriction portion for restricting rotations of a drive transmission member is known (for example, see Japanese Patent No. 5403864).

Japanese Patent No. 5403864 discloses an instrument sterile adaptor having an upper surface retractor plate (rotation restriction portion) provided with teeth for restricting rotations of a disk (drive transmission member). The instrument sterile adaptor is an adaptor through which a surgical instrument is attached to a robot arm. The robot arm includes a spring-loaded input unit (drive unit) that rotates the disk around a rotation axis. The surgical instrument is configured to be driven by the rotations of the disk rotated by the spring-loaded input unit of the robot arm.

The instrument sterile adaptor disclosed in Japanese Patent No. 5403864 is attached to the robot arm, by rotating the spring-loaded input unit in a state where the rotations of the disk by the spring-loaded input unit are stopped. Specifically, the disc includes teeth that are engaged with the teeth of the upper surface retractor plate.

Thus, in the device sterile adaptor, even if the disk rotates with the rotations of the spring-loaded input unit, the rotations of the disk are restricted by the engagement of the teeth of the disk with the teeth of the upper surface retractor plate. As a result, the instrument sterile adaptor is attached to the robot arm in the state where the rotations of the disk due to the rotations of the spring-loaded input unit is prevented.

SUMMARY

However, in the instrument sterile adaptor disclosed in Japanese Patent No. 5403864, the disk needs to be rotated in accordance with the rotation of the spring-loaded input unit of the robot arm in order to drive the surgical instrument. Therefore, it may be necessary to provide a structure and a space for disengaging the teeth of the disc from the teeth of the upper surface retractor plate after attaching the instrument sterile adaptor to the robot arm. For this reason, an extra internal structure and internal space may be needed in the sterile adaptor, so that it may be difficult to suppress a complexity and size of the structure of the sterile adaptor (adaptor main body) while preventing the disk (drive transmission member) from being rotated together with the rotations of the spring-loaded input unit (drive part).

An object of an aspect of one or more embodiments of this disclosure may be to provide a stopper and an adaptor capable of preventing a drive transmission member from rotating together with a drive part while preventing a complicated and enlarged structure of an adaptor main body.

A first aspect of the disclosure may be a stopper to be attached to an adaptor main body, wherein the adaptor main body is to be provided between a drive part provided at a robot arm and a surgical instrument and the adaptor main body includes a drive transmission member to transmit a driving force from the drive part to the surgical instrument.

The stopper according to the first aspect may include a stopper body; and a rotation restriction portion provided at the stopper body and configured to restrict rotations of the drive transmission member. The stopper is configured such that the rotation restriction portion restricts the rotations of the drive transmission member in a state where the stopper body is attached to the adaptor main body and the rotation restriction portion releases the restriction of the rotations of the drive transmission member in a state where the stopper body is detached from the adaptor main body.

A second aspect of the disclosure may be a stopper to be attached to an adaptor main body, wherein the adaptor main body is to be provided between a drive part provided at a robot arm and a surgical instrument and the adaptor main body includes a drive transmission member to transmit a driving force from the drive part to the surgical instrument.

The stopper according to the second aspect may include: a stopper body; a rotation restriction portion provided at the stopper body and configured to restrict rotations of the drive transmission member; and an attachment portion provided at the stopper body and configured to detachably attach the stopper body to the adaptor main body. The rotation restriction portion may restrict the rotations of the drive transmission member in a state where the stopper body is attached to the adaptor main body by the attachment portion.

A third aspect of the disclosure may be an adaptor including: an adaptor main body to be provided between a drive part provided at a robot arm and a surgical instrument and including a drive transmission member to transmit a driving force from the drive part to the surgical instrument; and a stopper to be attached to an adaptor main body.

In the adaptor according to the third aspect, the stopper may include: a stopper body; and a rotation restriction portion provided at the stopper body and configured to restrict rotations of the drive transmission member. The stopper is configured such that the rotation restriction portion restricts the rotations of the drive transmission member in a state where the stopper body is attached to the adaptor main body and the rotation restriction portion releases the restriction of the rotations of the drive transmission member in a state where the stopper body is detached from the adaptor main body.

BRIEF DESCRIPTION OF THE DRAWINGS

FIG. 9A is a diagram illustrating a perspective view of the drive part.

FIG. 9B is a diagram illustrating an exploded perspective view of the drive part.

DETAILED DESCRIPTION

Figure 1:
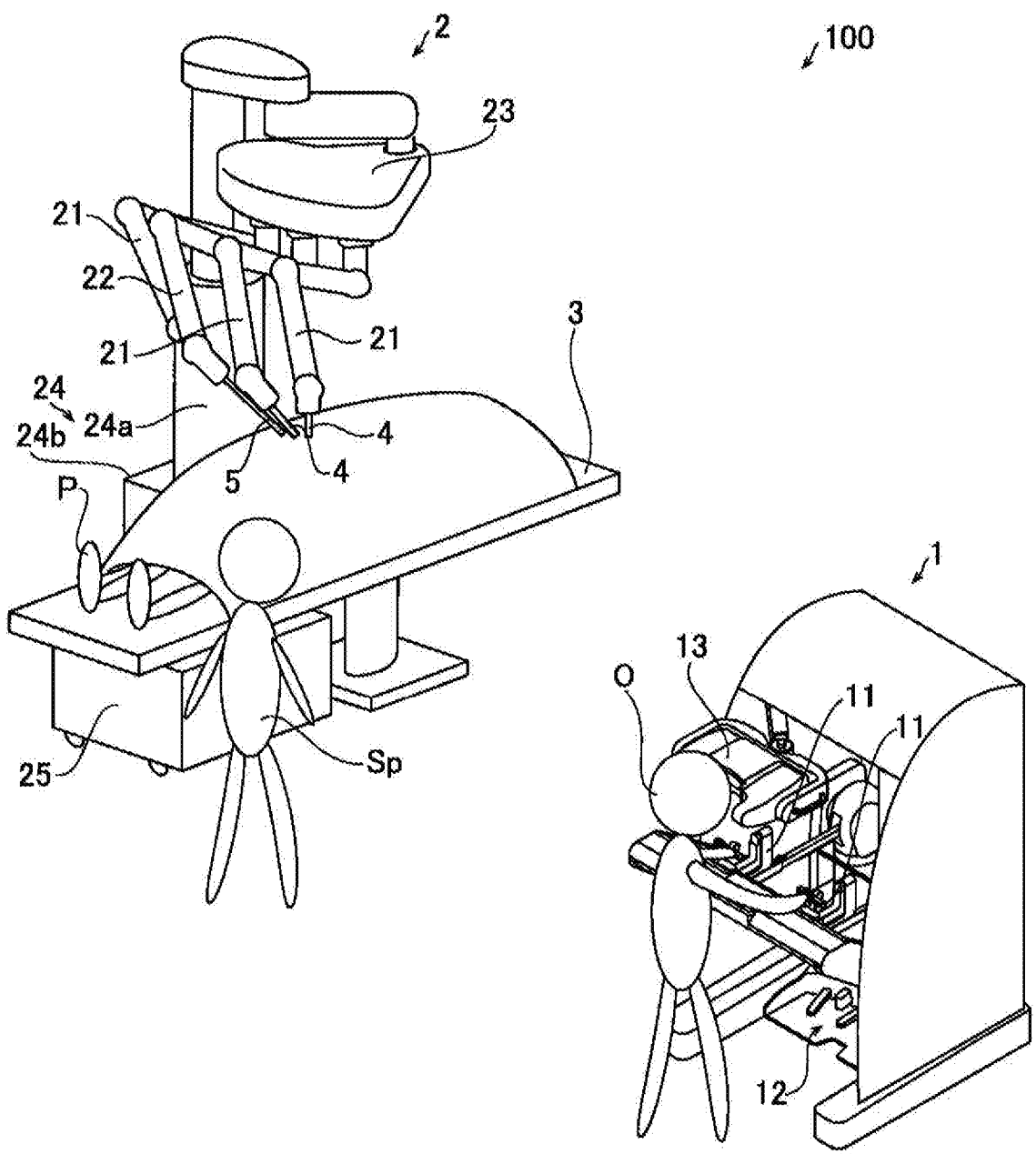
FIG. 1 is a diagram illustrating an overview of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

The configuration of a robotic surgical system 100 according to a first embodiment is described with reference to FIGS. 1 and 2.

As illustrated in FIG. 1, the robotic surgical system 100 includes a remote control apparatus 1 and a patient-side apparatus 2.

The remote control apparatus 1 is provided to remotely control medical equipment provided for the patient-side apparatus 2. When an operator O, as a surgeon, inputs an action mode instruction to be executed by the patient-side apparatus 2, to the remote control apparatus 1, the remote control apparatus 1 transmits the action mode instruction to the patient-side apparatus 2. In response to the action mode instruction transmitted from the remote control apparatus 1, the patient-side apparatus 2 operates medical equipment, including surgical instruments 4 attached to robot arms 21 and an endoscope 5 attached to a robot arm 22. This allows for minimally invasive surgery.

The patient-side apparatus 2 is positioned beside an operation table 3 on which the patient P is laid. The patient-side apparatus 2 constitutes an interface to perform a surgery for a patient P in response to an input from the remote control apparatus 1. The patient-side apparatus 2 includes plural robot arms 21 and 22, a platform 23, a positioner 24, and a controller 25.

Each of the plural robot arms 21 includes plural joints. Each joint includes a driver provided with a servo-motor and a position detector such as an encoder. The robot arms 21 are configured so that the medical equipment attached to each robot arm 21 is controlled by a driving signal given through the controller 25 and performs a desired movement. Note that the robot arm 22 has a configuration same as the robot arm 21.

The surgical instruments 4 as the medical equipment are detachably attached to the distal end portions of the robot arms 21. In surgeries using the patient-side apparatus 2, the robot arms 21 introduce the surgical instruments 4 into the body of the patient P through a cannula (trocar) placed on the body surface of the patient P.

Each surgical instrument 4 includes: a housing 41 (see FIG. 3), which is attached to the robot arm 21; an elongated shaft 42 (see FIG. 3); and an end effector 43 (see FIG. 3), which is provided at the distal end portion of the shaft 42.

The end effector 43 may be grasping forceps, scissors, a hook, a high-frequency knife, a snare wire, a clamp, or a stapler, for example. The end effector 43 is not limited to those and can be various types of treatment tools. The end effector 43 of the surgical instrument 4 is then located near the surgery site.

To the distal end of the robot arm 22, the endoscope 5 as the medical equipment is detachably attached. The endoscope 5 captures an image within the body cavity of the patient P. The captured image is outputted to the remote control apparatus 1. The endoscope 5 is a 3D endoscope capable of capturing a three-dimensional image or a 2D endoscope. In surgeries using the patient-side apparatus 2, the robot arm 22 introduces the endoscope 5 into the body of the patient P through a trocar placed on the body surface of the patient P. The endoscope 5 is then located near the surgery site.

The platform 23 commonly supports the robot arms 21 and the robot arm 22. The positioner 24 is placed on the floor of an operation room and supports the platform 23. The positioner 24 includes a column 24a including an elevating shaft adjustable in the vertical direction and a base 24b including wheels and thus being movable on the floor surface.

The remote control apparatus 1 constitutes the interface with the operator O. The remote control apparatus 1 is an apparatus that allows the operator O to operate the surgical instruments 4 attached to the robot arms 21 and the endoscope 5 attached to the robot arm 22. Specifically, the remote control apparatus 1 is configured to transmit action mode instructions which are inputted by the operator O and are to be executed by the surgical instruments 4 and endoscope 5, to the patient-side apparatus 2 through the controller 25. The remote control apparatus 1 is installed beside the operation table 3 so that the operator O can see the condition of the patient P very well while operating the remote control apparatus 1, for example. The remote control apparatus 1 may be configured to transmit action mode instructions wirelessly and installed in a room different from the operation room where the operation table 3 is installed.

The action modes to be executed by the surgical instruments 4 include modes of actions to be taken by each surgical instrument 4 (a series of positions and postures) and actions to be executed by the function of each surgical instrument 4. When the surgical instrument 4 is a pair of grasping forceps, for example, the action modes to be executed by the surgical instrument 4 include roll and pitch positions of the wrist of the end effector 43 and actions to open and close the jaws. When the surgical instrument 4 is a high-frequency knife, the action modes to be executed by the surgical instrument 4 may include vibration of the high-frequency knife, specifically, supply of current to the high-frequency knife. When the surgical instrument 4 is a snare wire, the action modes to be executed by the surgical instrument 4 may include a capturing action and an action to release the captured object. Further the action modes may include an action to supply current to a bipolar or monopolar instrument to burn off the surgery site.

The action modes to be executed by the endoscope 5 include, for example, an action mode to move the position and posture of the distal end of the endoscope 5 and an action mode to set the zoom magnification, for example.

Figure 2:
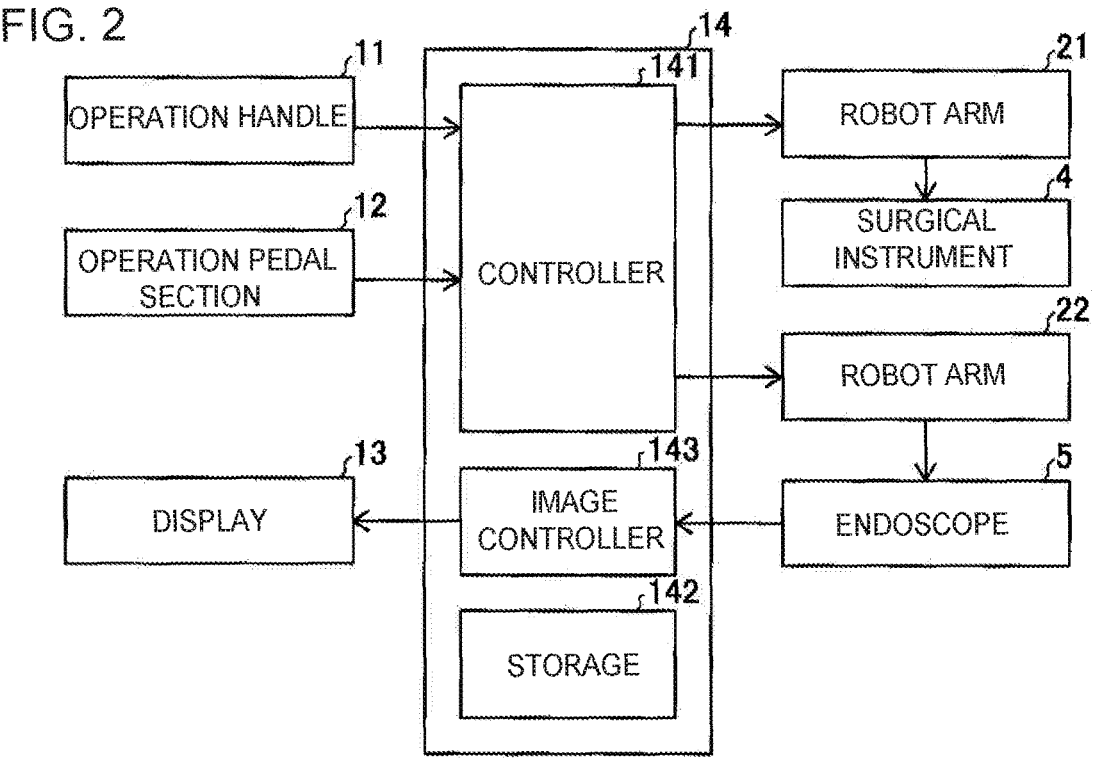
FIG. 2 is a block diagram illustrating a view of a control-related configuration of the robotic surgical system according to a first embodiment.

As illustrated in FIGS. 1 and 2, the remote control apparatus 1 includes operation handles 11, an operation pedal section 12, a display part 13, and a control apparatus 14.

The operation handles 11 are provided in order to remotely operate medical equipment (surgical instruments 4 and the endoscope 5) attached to the robot arms 21 and 22. Specifically, the operation handles 11 accept operations by the operator O for operating the medical equipment. The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 1 toward the front side. The operation handles 11 are configured to move in a predetermined three-dimensional operation region. Specifically, the operation handles 11 are configured so as to move up and down, right and left, and forward and rearward.

The remote control apparatus 1 and patient-side apparatus 2 constitute a master-slave system in terms of controlling movement of the robot arms 21 and 22. The operation handles 11 constitute an operating part on the master side in the master-slave system. The robot arms 21 and 22 holding medical equipment constitute an operating section on the slave side. When the operator O operates the operation handles 11, the movement of the robot arms 21 or 22 is controlled so that the distal end portions (the end effectors 43 of the surgical instruments 4) of the robot arms 21 or the distal end portion (the endoscope 5) of the robot arm 22 moves following the movement of the operation handles 11.

The patient-side apparatus 2 controls the movement of the robot arms 21 in accordance with the set motion scaling ratio. When the motion scaling ratio is set to 1/2, for example, the end effectors 43 of the surgical instruments 4 move 1/2 of the movement distance of the operation handles 11. This allows for precise fine surgery.

The operation pedal section 12 includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 4 to coagulate a surgery site. Specifically, when the coagulation pedal is operated, voltage for coagulation is applied to the surgical instrument 4 to coagulate a surgery site. The cutting pedal enables the surgical instrument 4 to cut a surgery site. Specifically, the cutting pedal is operated to apply voltage for cutting to the surgical instrument 4 and cut a surgery site.

The camera pedal is used to control the position and orientation of the endoscope 5 that captures images within the body cavity. Specifically, the camera pedal enables operation of the endoscope 5 by the operation handles 11. The position and orientation of the endoscope 5 are controllable by the operation handles 11 while the camera pedal is being pressed. The endoscope 5 is controlled by using both of the right and left operation handles 11, for example. Specifically, when the operator O rotates the right and left operation handles 11 about the middle point between the right and left operation handles 11, the endoscope 5 is rotated. When the operator O presses the right and left operation handles 11 together, the endoscope 5 goes forward into the body cavity. When the operator O pulls the right and left operation handles 11 together, the endoscope 5 goes back. When the operator O moves the right and left operation handles 11 together up, down, right, or left, the endoscope 5 moves up, down, right, or left, respectively.

The clutch pedal is used to temporarily disconnect operation-related connection between the operation handles 11 and the robot arms 21 and 22 to stop movement of the surgical instruments 4. Specifically, when the clutch pedal is being pressed, the robot arms 21 and 22 of the patient-side apparatus 2 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21 and 22. The operator O restarts the operation for the operation handles 11 around the center thereof.

The display part 13 or a display is configured to display images captured by the endoscope 5. The display part 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 5 attached to the robot arm 22 of the patient-side apparatus 2. When the non-scope type display section is attached, the non-scope type display section also displays 3D images captured by the endoscope 5 provided for the patient-side apparatus 2. The non-scope type display section may display 2D images captured by the endoscope 5 provided for the patient-side apparatus As illustrated in FIG. 2, the control apparatus 14 includes a controller 141, a storage 142, and an image controller 143, for example. The controller 141 includes a calculator such as a CPU. The storage 142 includes a memory, such as a ROM (Read Only Memory) and a RAM (Random Access Memory).

The control apparatus 14 may be composed of a single controller performing centralized control or may be composed of plural controllers that perform decentralized control in cooperation with each other.

The controller 141 determines whether an action mode instruction inputted by the operation handles 11 is to be executed by the surgical instruments 4 or to be executed by the endoscope 5, depending on the state of the operation pedal section 12. When determining that the action mode instruction inputted by the operation handles 11 is to be executed by any one of the surgical instruments 4, the controller 141 transmits the action mode instruction to the corresponding robot arm 21. The robot arm 21 is thereby driven for controlling movement of the surgical instrument 4 attached to the robot arm 21.

When determining that the action mode instruction inputted by the operation handles 11 is to be executed by the endoscope 5, the controller 141 transmits the action mode instruction to the robot arm 22. The robot arm 22 is thereby driven for control of movement of the endoscope 5 attached to the robot arm 22.

The storage 142 stores control programs corresponding to the types of the surgical instrument 4, for example. The controller 141 reads the stored control programs according to the types of the attached surgical instruments 4. The action mode instruction from at least one of the operation handles 11 and the operation pedal section 12 of the remote control apparatus 1 thereby cause the respective surgical instruments 4 to perform proper movements.

The image controller 143 transmits images acquired by the endoscope 5 to the display part 13. The image controller 143 performs processing and alternations for the images when needed.

(Configuration of Surgical Instrument, Adaptor, Drape, and Robot Arm)

With reference to FIGS. 3 to 14, the configurations of the surgical instrument 4, the adaptor 6 including an adaptor main body 6a, a drape 7, and the robot arm 21 are described.

Here, the direction in which the surgical instrument 4 (the direction in which the shaft 42 extends) is defined as a Y direction, the distal side of the surgical instrument 4 along the Y direction is defined as a Y1 direction, and the opposite side of the Y1 direction is defined as a Y2 direction. The direction in which the surgical instrument 4 and the adaptor 6 are adjacent to each other is defined as a Z direction, the surgical instrument 4 side along the Z direction is defined as a Z1 direction, and the opposite side of the Z1 direction is defined as a Z2 direction. Further, the direction orthogonal to the Y direction and the Z direction is defined as an X direction, one side along the X direction is defined as an X1 direction, and the other side along the X direction is defined as an X2 direction.

(Attached State)

Figure 3:
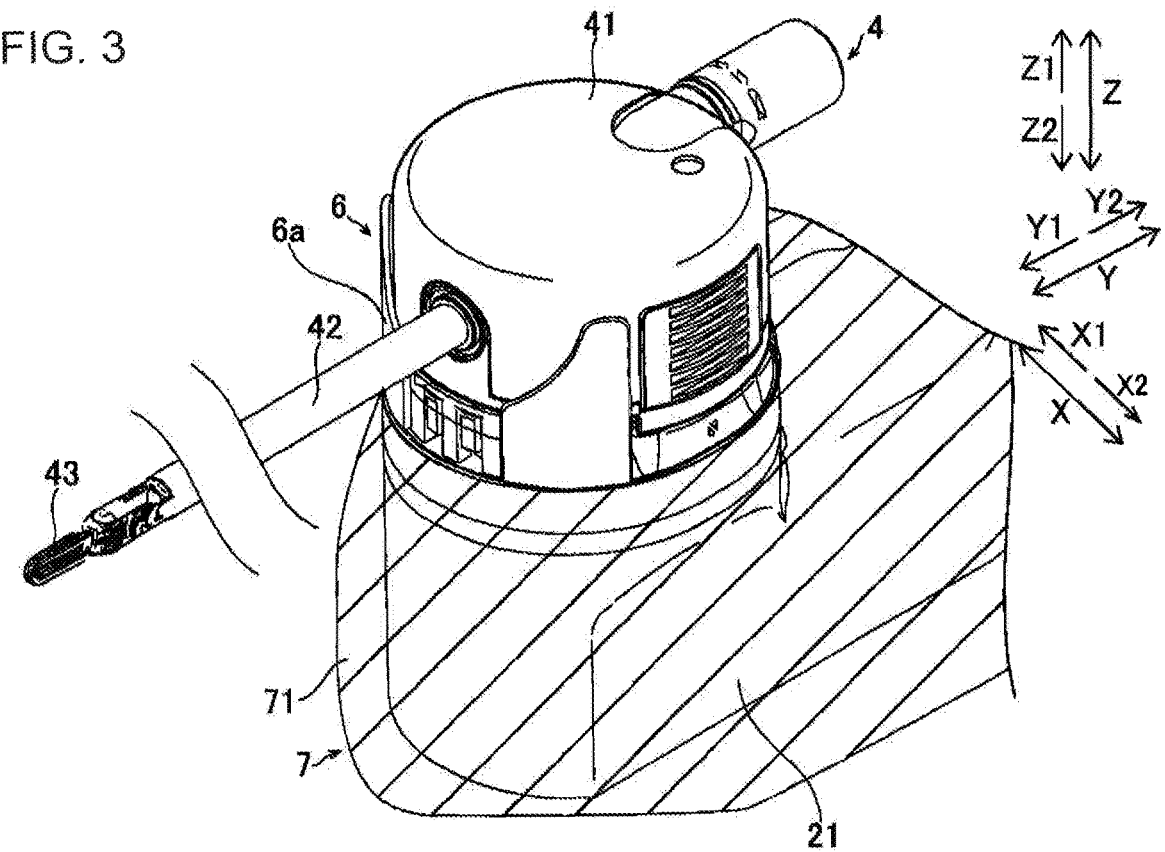
FIG. 3 is a diagram illustrating a perspective view of a state where a surgical instrument is attached to a robot arm via an adaptor according to a first embodiment.
Figure 4:
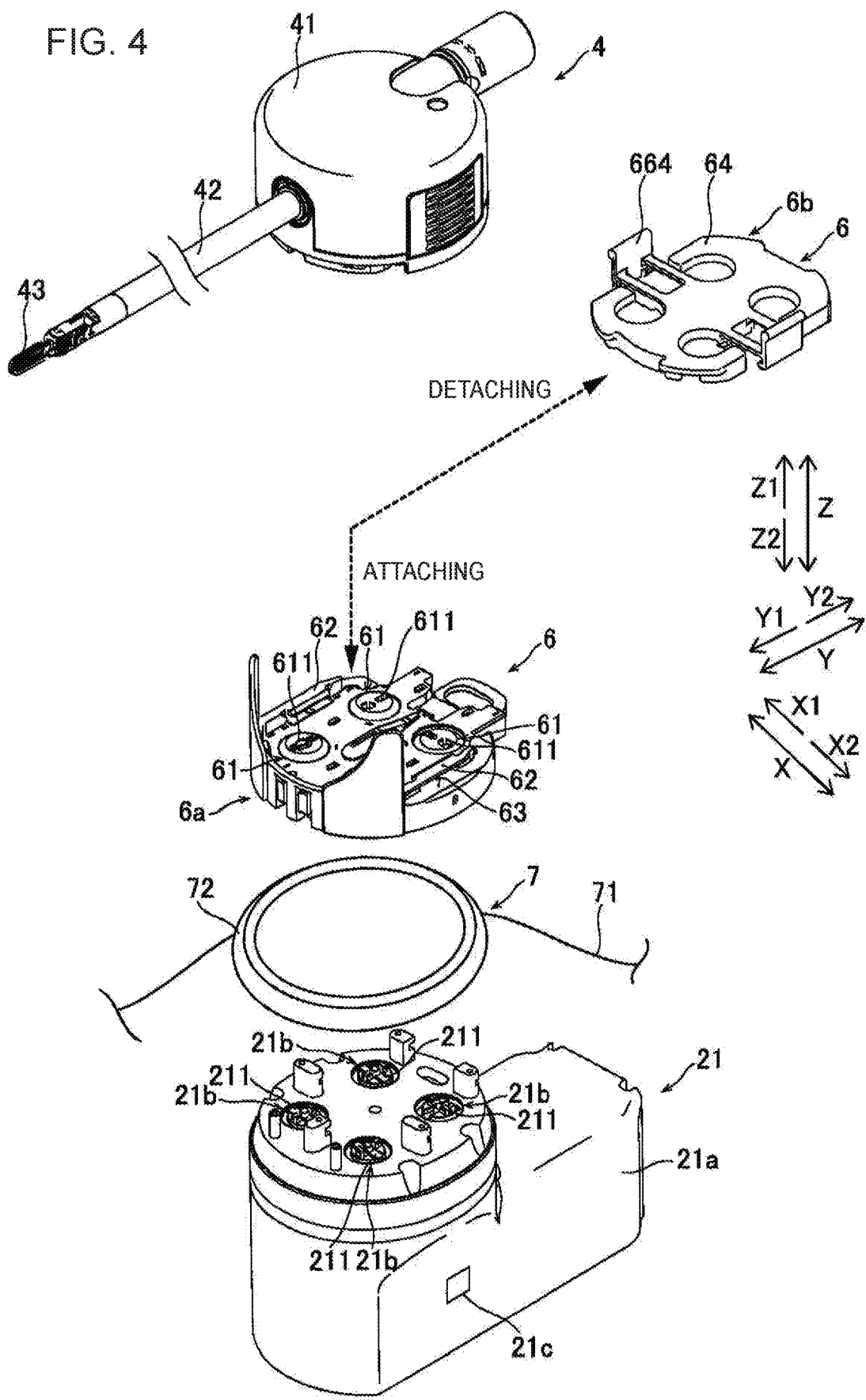
FIG. 4 is a diagram illustrating a perspective view of a state where the surgical instrument is to be attached to the robot arm via the adaptor according to a first embodiment.

As illustrated in FIGS. 3 to 4, the surgical instrument 4 is detachably connected to the robot arm 21 through the adaptor main body 6a. The adaptor main body 6a is a drape adaptor configured to sandwich a sterile drape 7 to cover the robot arm 21, between the robot arm 21 and the adaptor main body 6a. That is, the adaptor main body 6a is configured such that the drape 7 is attachable to the adaptor main body 6a. With this configuration, when the adaptor main body 6a is attached to drive parts 21b of the robot arm 21, the drape 7 is attached between the adaptor main body 6a and the drive parts 21b, so as to securely separate a clean area from a contaminated area.

The surgical instrument 4 is attached to the Z1 side of the adaptor main body 6a. The adaptor main body 6a is attached to the Z1 side of the robot arm 21.

The robot arm 21 is used in the clean area and is thus covered with the drape 7. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O and an assistant Sp (see FIG. 1), make sure that only sterile objects are placed in the clean area during surgery and perform sterilization for an object which is to be moved to the clean area from the contaminated area. Similarly, when the assistant Sp, as one of the members of the surgical team including the operator O, place their hands in the contaminated area, the members sterilize their hands before directly touching objects located in the clean area. Instruments used in the clean area are sterilized or are covered with sterile drape 7.

As illustrated in FIG. 4, the drape 7 includes a body section 71 that covers the robot arm 21 and an attachment section 72 sandwiched between the robot arm 21 and the adaptor main body 6a. The body section 71 is made of a flexible film member. The flexible film member is made of a resin material, such as thermoplastic polyurethane and polyethylene. The body section 71 includes an opening so that the robot arm 21 is engaged with the adaptor main body 6a. In the opening of the body section 71, the attachment section 72 is provided so as to close the opening. The attachment section 72 is made of a resin mold member. The resin mold member is made of a resin member such as polyethylene terephthalate. The attachment section 72 is harder (less flexible) than the body section 71. The attachment section 72 includes an opening so that the robot arm 21 is engaged with the adaptor main body 6a. The opening of the attachment section 72 may be provided corresponding to the section where the robot arm 21 is engaged with the adaptor main body 6a. The opening of the attachment section 72 may include plural openings corresponding to plural sections at which the robot arm 21 is engaged with the adaptor main body 6a.

Figure 5:
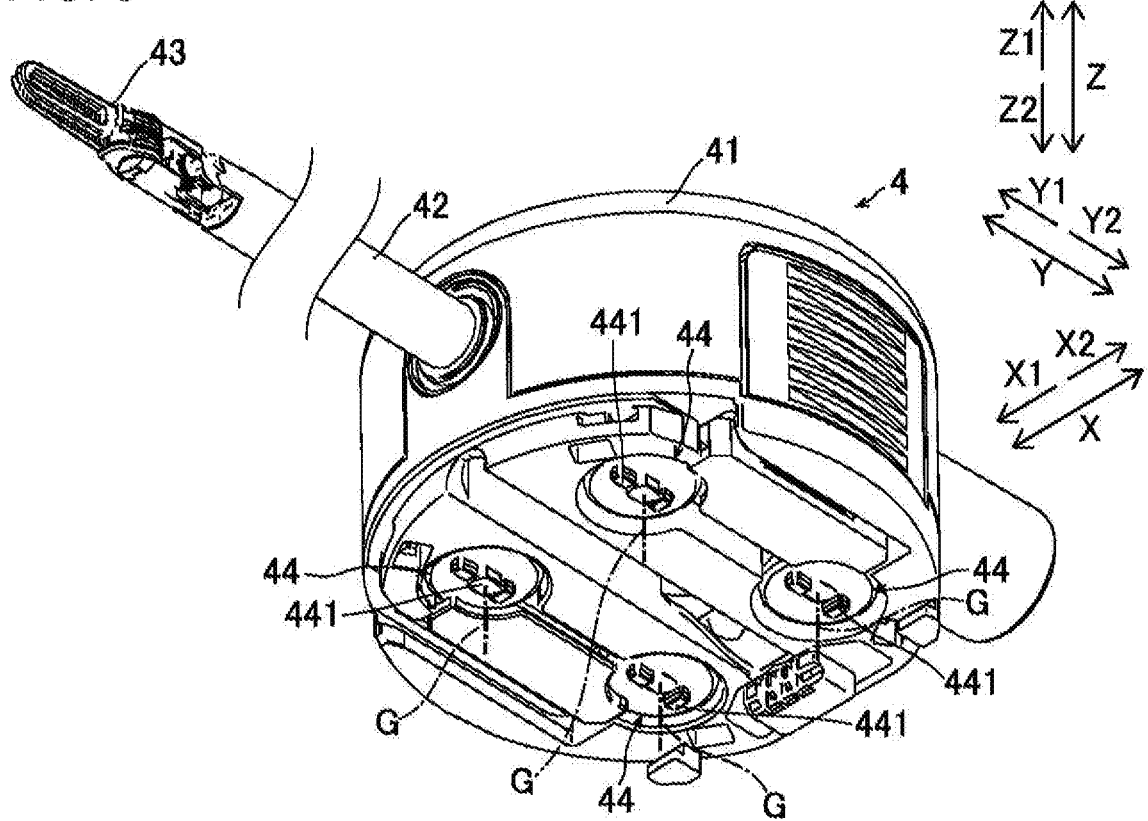
FIG. 5 is a diagram illustrating a perspective view of the surgical instrument according to a first embodiment.

As illustrated in FIGS. 4 and 5, the surgical instrument 4 includes plural (four) driven members 44. The driven members 44 are provided within the housing 41 and are rotatable about the respective rotation axes G extending along the Z axis. The plural driven members 44 are provided to operate (drive) the end effector 43. For example, the driven members 44 are connected to the end effector 43 with wires (not illustrated) inserted through the shaft 42. With this, rotations of the driven members 44 drive the wires, which operate (drive) the end effector 43. In addition, the driven member 44 is connected to the shaft 42 through gears (not illustrated), for example. With this, the shaft 42 is rotated with rotation of the driven member 44.

To transmit driving forces from the robot arm 21 to the end effector 43, the driven members 44 include engagement projections 441, which are engaged with later-described drive transmission members 61 of the adaptor main body 6a. The engagement projections 441 protrude from the Z2-side surfaces of the respective driven members 44 toward the adaptor main body 6a (in the Z2 direction). The engagement projections 441 have shapes corresponding to later-described engagement recesses 611 (see FIG. 4) of the adaptor main body 6a, respectively. The engagement recess 611 is an example of a drive transmission recess.

Figure 6:
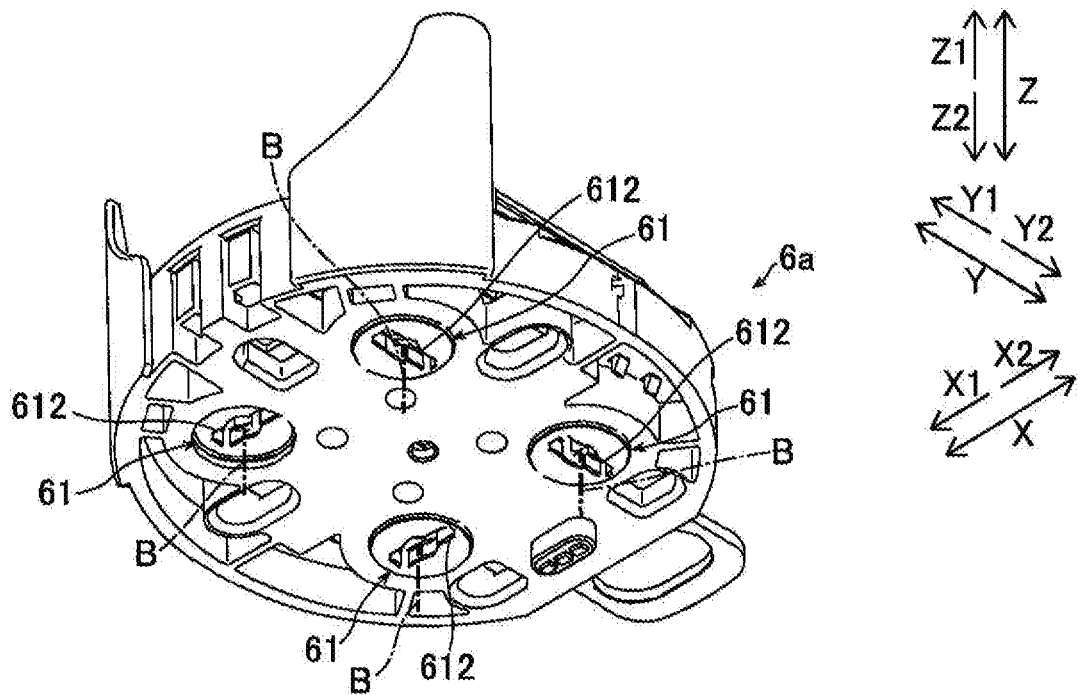
FIG. 6 is a diagram illustrating a perspective view of an adaptor main body according to the first embodiment.

As illustrated in FIGS. 4 and 6, the adaptor main body 6a includes plural (four) drive transmission members 61 and a pair of guide rails 62. The drive transmission members 61 are configured to transmit driving forces from the robot arm 21 to the driven members 44 of the surgical instrument 4. That is, the drive transmission members 61 are provided so as to correspond to the driven members 44 of the surgical instrument 4. The drive transmission members 61 are rotatable about the respective rotation axes B, which extend along the Z direction.

As illustrated in FIG. 4, each of drive transmission members 61 includes the engagement recess 611 which is respectively engaged with the engagement projection 441 of the corresponding driven member 44. The engagement recess 611 is located at the surgical instrument 4 side (the Z1 side) of the drive transmission member 61 and is recessed from the Z1 side surface of the drive transmission member 61, toward the Z2 direction, opposite to the surgical instrument 4.

As illustrated in FIG. 6, each of the drive transmission members 61 includes an engagement recess 612, which is engaged with a later-described engagement projection 211 of the corresponding drive part 21b of the robot arm 21. The engagement recess 612 is located at the robot arm 21 side (the Z2 side) of the drive transmission member 61. The engagement recess 612 is recessed from the Z2 side surface of the drive transmission member 61, toward the Z1 direction, opposite to the robot arm 21. The plural drive transmission members 61 include substantially the same configuration.

Figure 7A:
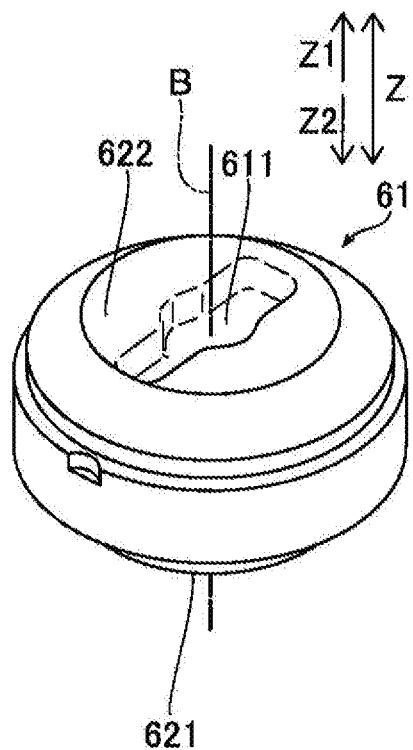
FIG. 7A is a diagram illustrating a perspective view of a drive transmission member.
Figure 7B:
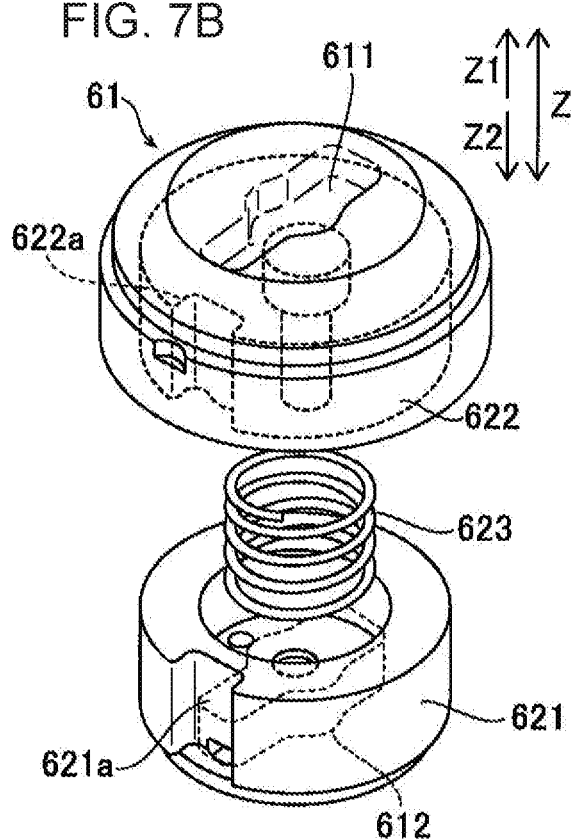
FIG. 7B is a diagram illustrating an exploded perspective view of the drive transmission member.

As illustrated in FIGS. 7A and 7B, each of the drive transmission members 61 includes a first member 621, which includes the engagement recess 612, and a second member 622, which includes the engagement recess 611. The first member 621 is located on the robot arm 21 side (the Z2 side) with respect to the second member 622 and the second member 622 is located on the surgical instrument 4 side (the Z1 side) with respect to the first member 621.

The first member 621 and the second member 622 accommodate a spring 623 therebetween. The spring 623 biases the first member 621 toward the Z2 side and the second member 622 toward the Z1 side. The spring 623 is a compression spring (a compression coil spring). The first member 621 is movable along the Z direction relative to the second member 622 with the spring 623 therebetween. The second member 622 is movable along the Z direction relative to the first member 621 with the spring 623 therebetween.

The first member 621 and the second member 622 are integrally rotated with each other about the rotational axis B extending the Z direction. Specifically, the first member 621 includes an engagement recess 621a that is engaged with the second member 622 with respect to the rotational direction, and the second member 622 includes an engagement protrusion 622a that is engaged with the first member 621 with respect to the rotational direction.

As illustrated in FIG. 4, the pair of guide rails 62 is configured to guide a sliding movement of the surgical instrument 4 in the Y1 direction upon attaching the surgical instrument 4 to the adaptor main body 6a. Specifically, the pair of guide rails 62 is provided on the Z1 side surface 63 of the adaptor main body 6a. The pair of guide rails 62 is provided to extend along the Y direction. The guide rails 62 are opposed to each other in the X direction.

Figure 8:
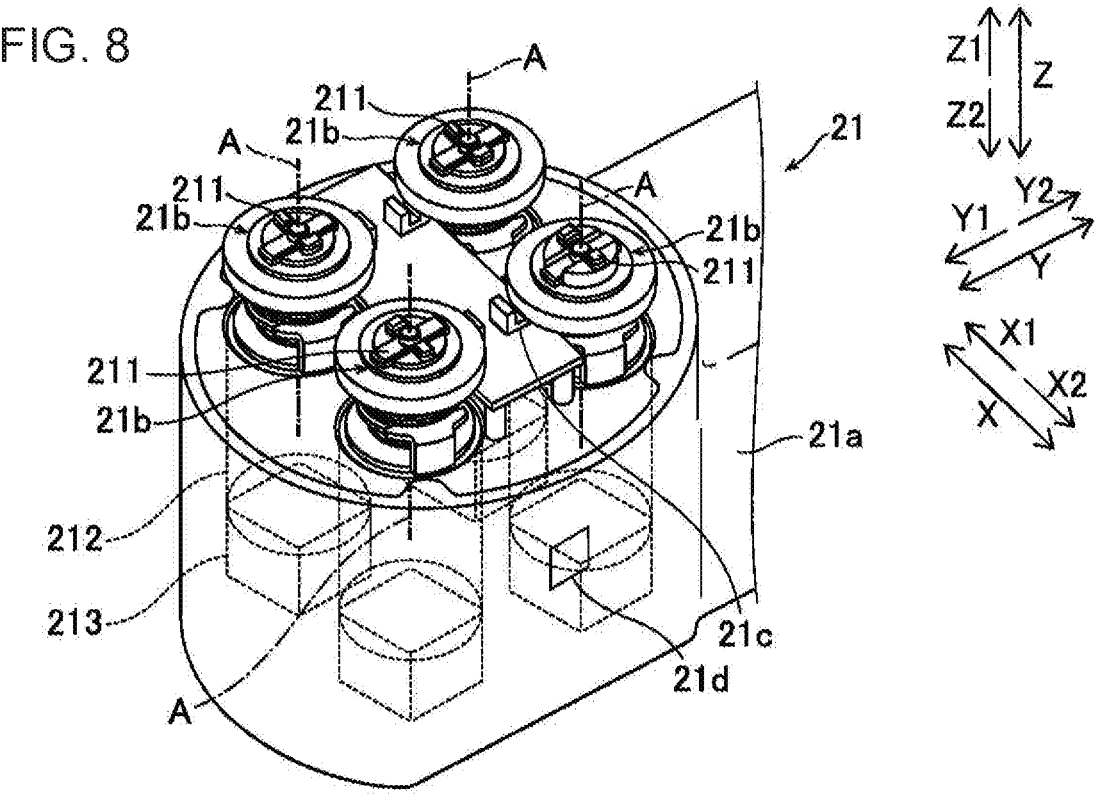
FIG. 8 is a diagram illustrating a perspective view of a drive part of the robot arm according to a first embodiment.

As illustrated in FIGS. 4 and 8, the robot arm 21 includes a frame 21a, a plurality (four) of the drive parts 21b, an optical sensor 21c, and a lamp 21d. Each of the drive parts 21b is attached to the frame 21a of the robot arm 21. The plural drive parts 21b are provided corresponding to the plural (four) drive transmission members 61 of the adaptor main body 6a. Each of the drive parts 21b has the same or a similar configuration, and thus only one of the drive parts 21b is described below to avoid redundancy.

As illustrated in FIGS. 9A and 9B, the drive part 21b includes the engagement projection 211, an actuator 212, a detection member 213, a spring 214, and an encoder 215.

The detection member 213 is provided to be detected by the optical sensor 21c. That is, the detection member 213 moves along with the movement of the second member 622 (see FIG. 7B) of the drive transmission member 61 in the Z direction. The detection member 213 includes a light blocking part 213a that blocks light emitted from the optical sensor 21c when the second member 622 of the drive transmission member 61 is moved in the Z2 direction. The light blocking part 213a is provided on an outer periphery of the detection member 213. The light blocking part 213a protrudes along the Z2 direction. Note that the light blocking part 213a does not block the light emitted from the optical sensor 21c when the second member 622 of the drive transmission member 61 is moved in the Z1 direction.

The engagement projection 211 of each drive part 21b is engaged with the engagement recess 612 of the corresponding drive transmission member 61 (see FIG. 6). The engagement projection 211 projects from the Z1 side surface of the drive part 21b toward the Z1 direction (the adaptor main body 6a side).

The actuator 212 includes a motor. The actuator 212 is configured to rotate the engagement projection 211 about the rotational axis A. Thereby, the drive transmission member 61 of the adaptor main body 6a engaged with the engagement projection 211 can be rotated about the rotational axis A extending in the Z direction, and the driven member 44 of the surgical instrument 4 engaged with the drive transmission member 61 can be rotated about the rotational axis A.

The encoder 215 detects the rotation angle of the shaft of the motor of the actuator 212. The encoder 215 is used to detect the rotation speed of the shaft based on the rotation angle of the shaft. An absolute rotary encoder is preferably used as the encoder 215 to detect the current rotation angle of the shaft of the motor.

Here, the controller 141 is able to detect the completion of the engagement between the robot arm 21 and the adaptor main body 6a based on a change in the rotation speed based on the rotation angle of the shaft of the motor detected by the encoder 215. For example, when the rotation speed of the shaft of the motor detected by the encoder 215 becomes equal to or less than a threshold value (for example, 5 [rpm]), the controller 141 detects (determines) that the completion of the engagement between the robot arm 21 and the adaptor main body 6a.

Figure 10A:
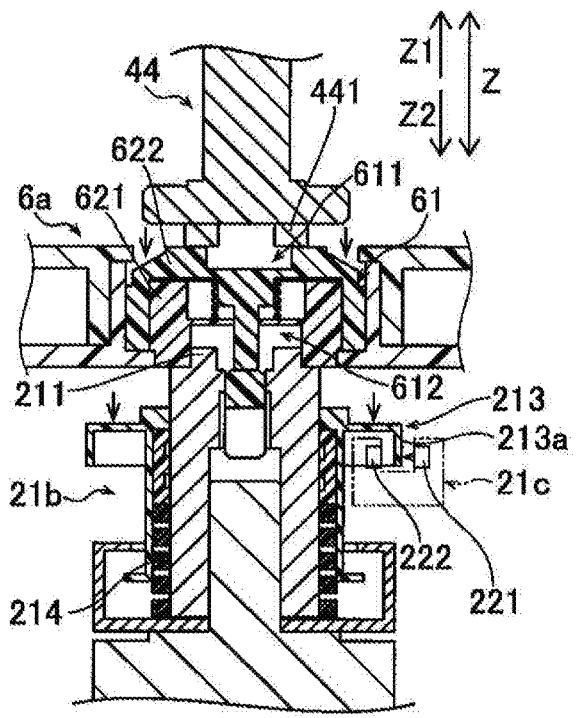
FIG. 10A is a diagram illustrating a cross-sectional view of a state where the surgical instrument and the adaptor are not engaged.
Figure 10B:
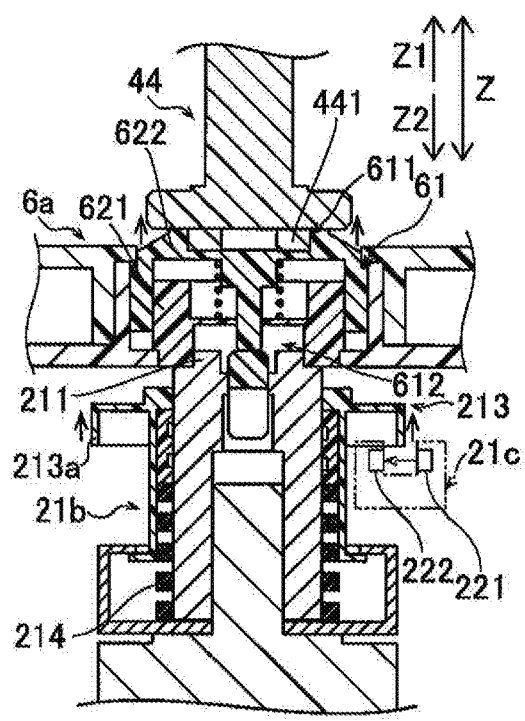
FIG. 10B is a diagram illustrating a cross-sectional view of a state where the surgical instrument and the adaptor are completely engaged.

As illustrated in FIGS. 10A and 10B, the optical sensor 21c can detect the completion of the engagement between the adaptor main body 6a and the surgical instrument 4, by using the change in the amount of received light according to the movement of the detection member 213 in the Z direction. For example, the optical sensor 21c may be a light transmission type sensor including a light emission part 221 that emits light and a light reception part 222 that receives the light from the light emission part 221.

When the light blocking part 213a of the detection member 213 moves in the Z direction along with the movement of the detection member 213 in the Z direction, which makes the optical sensor 21c transitioning from a light-blocked state to a light-unblocked state, the optical sensor 21c detects the completion of the engagement between the adaptor main body 6a and the surgical instrument 4. Specifically, as illustrated in FIG. 10A, when the engagement projection 441 and the engagement recess 611 are not engaged and the second member 622 is located in the Z2 side, the light emitted from the light emission part 221 toward the light reception part 222 is blocked by the light blocking part 213a. Thus, the optical sensor 21c detects incompletion of the engagement between the adaptor main body 6a and the surgical instrument 4. In contrast, as illustrated in FIG. 10B, when the engagement projection 441 and the engagement recess 611 are engaged and the second member 622 is located in the Z1 side, the light irradiated from the light emission part 221 toward the light reception part 222 is not blocked by the light blocking part 213a. Thus, the optical sensor 21c detects the completion of the engagement between the adaptor main body 6a and the surgical instrument 4. Note that the optical sensor 21c is configured to detect High when the light is received and to detect Low when the light is blocked.

The lamp 21d is configured to change the lighting state thereof depending on the detection result of either the completion of engagement between the robot arm 21 and the adaptor main body 6a or the completion of engagement between the adaptor main body 6a and the surgical instrument 4.

Specifically, the lamp 21d is configured to be turned on (to emit light) when the engagement between the robot arm 21 and the adaptor main body 6a is completed, and to be turned off (to emit no light) when the robot arm 21 and the adaptor main body 6a are not yet completely engaged. Note that the lamp 21d is configured to be turned on (to emit light) when the engagement between the robot arm 21 and the adaptor main body 6a is completed and then turned off (to emit no light).

The lamp 21d is configured to be turned on (to emit light) when the adaptor main body 6a and the surgical instrument 4 are completely engaged, and to be turned off (to emit no light) when the adaptor main body 6a and the surgical instrument 4 are not yet completely engaged. Note that the lamp 21d is configured to be turned on (to emit light) when the engagement between the adaptor main body 6a and the surgical instrument 4 is completed and then turned off (to emit no light).

Note that the lamp 21d may be configured to emit light of a first color such as green when both of the engagement between the robot arm 21 and the adaptor main body 6a and the engagement between the adaptor main body 6a and the surgical instrument 4 are completed, and be configured to emit light of a second color such as red different from the first color, instead of turning off the light, when neither of the engagement between the robot arm 21 and the adaptor main body 6a nor the engagement between the adaptor main body 6a and the surgical instrument 4 are completed. In addition, the lamp 21d may be configured such that a color of the light emitted from the lamp 21d when the engagement between the robot arm 21 and the adaptor main body 6a is completed is different from a color of the light emitted from the lamp 21d when the engagement between the adaptor main body 6a and the surgical instrument 4 is completed.

(Configuration of Stopper)

As illustrated in FIG. 4, the adaptor 6 is provided between the drive parts 21b and the surgical instrument 4 and includes the adaptor main body 6a and a stopper 6b to be attached to the adaptor main body 6a. The adaptor main body 6a includes the drive transmission members 61, which are rotated to transmit the driving forces from the drive parts 21b to the surgical instrument 4.

Figure 11:
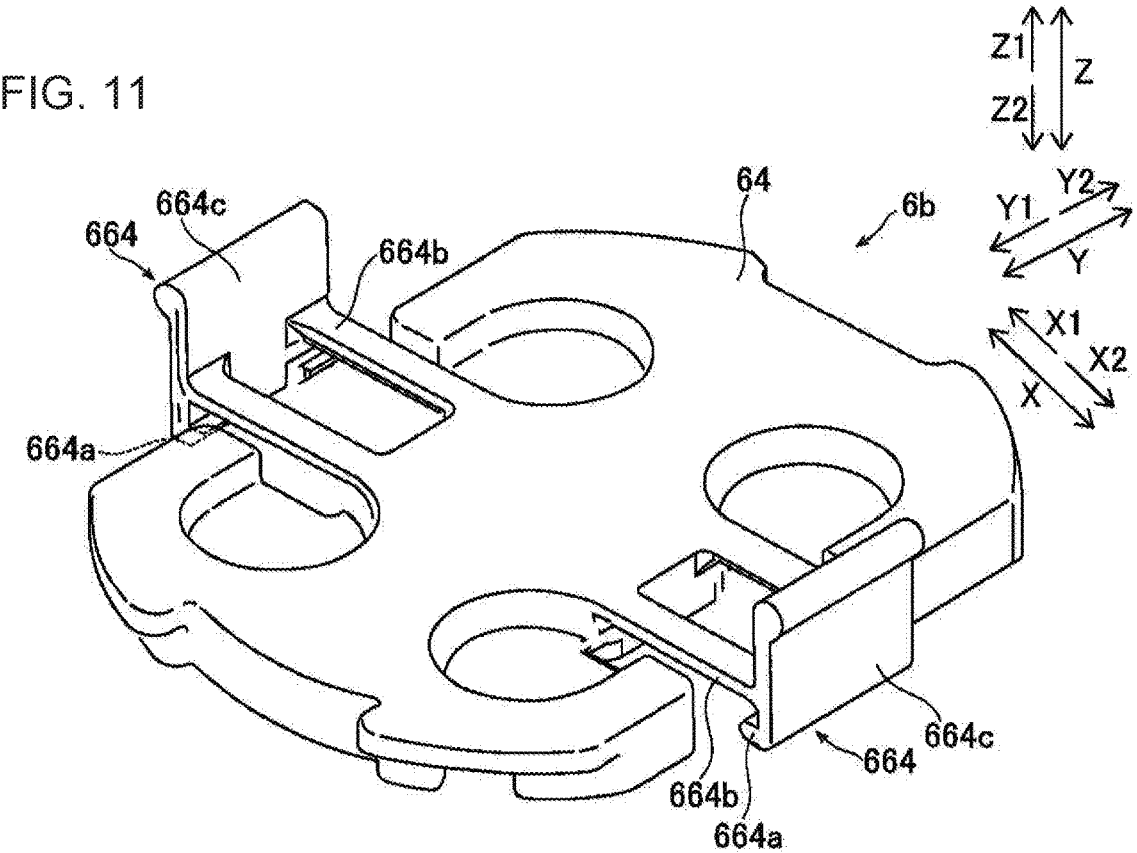
FIG. 11 is a diagram illustrating a perspective view of a stopper according to a first embodiment as viewed from the Z1 side.
Figure 12:
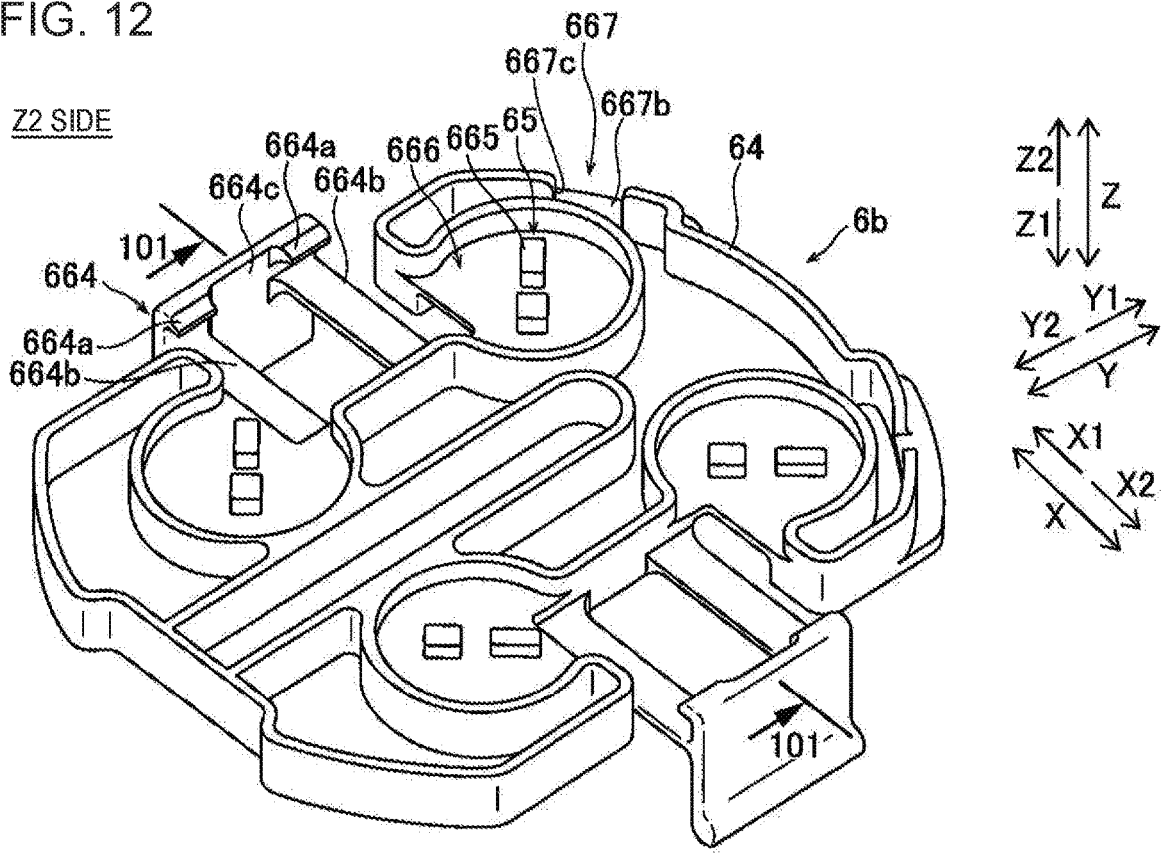
FIG. 12 is a diagram illustrating a perspective view of the stopper according to a first embodiment as viewed from the Z2 side.

As illustrated in FIGS. 11 and 12, the stopper 6b is configured to hold the adaptor main body 6a with fixing (positionally-fixing) rotational positions (rotational angles) of the drive transmission members 61 of the adaptor main body 6a (see FIG. 4). The positionally-fixing may indicate fixing and retaining the rotational positions (the rotational angles) of the drive transmission members 61.

Specifically, the stopper 6b includes a stopper body 64 and rotation restriction portions 65 provided on the stopper body 64 to regulate the rotations of the drive transmission members 61 (see FIG. 4). The stopper body 64 is configured to be attached to the adaptor main body 6a with the rotation restriction portions 65 restricting the rotations of the drive transmission members 61, upon an operation of attaching the adaptor main body 6a of the adaptor 6 to the drive parts 21b (see FIG. 4) of the robot arm 21. The stopper body 64 is also configured to be detached from the adaptor main body 6a after the adaptor main body 6a of the adaptor 6 is attached to the drive parts 21b of the robot arm 21. That is, the stopper 6b is detached from the adaptor main body 6a, upon attaching the surgical instrument 4 to the drive part 21b of the robot arm 21 via the adaptor main body 6a. Accordingly, the adaptor main body 6a itself does not need to have a structure for regulating the rotations of the drive transmission members 61. Therefore, without providing an extra internal structure and/or an extra internal space in the adaptor main body 6a, the rotations of the drive transmission members 61 can be restricted by the rotation restriction portions 65 of the stopper 6b. With this configuration, the rotations of the drive transmission members 61 due to the rotations of the drive parts 21b can be prevented, while preventing a complicated and enlarged structure of the adaptor main body 6a.

The stopper body 64 is formed of a resin material such as polypropylene. The stopper body 64 is formed with a reduced thickness. When viewed from the Z1 side, the stopper body 64 has a shape corresponding to the Z1 side surface 63 (see FIG. 4) of the adaptor main body 6a. The Z1 side surface 63 of the stopper body 64 is formed in a substantially planar shape. The Z2 side surface of the stopper body 64 has projections and recesses to reduce the thickness.

(Configuration of Attachment Portion)

The stopper body 64 includes an attachment portion 664 for detachably attaching the stopper body 64 to the adaptor main body 6a (see FIG. 4). The attachment portion 664 and the rotation restriction portions 65, both of which are provided in the stopper body 64, are separately provided. Thus, unlike a case where the rotation restriction portions 65 also have the function of the attachment portion 664, the rotation restriction portions 65 of the stopper 6b can be simplified.

In other words, the attachment portion 664 is configured to attach the stopper body 64 to the adaptor main body 6a with fixing the position of the stopper body 64 with respect to the adaptor main body 6a, and to detach the stopper body 64 from the adaptor main body 6a with releasing the fixation of the position of the stopper body 64 with respect to the adaptor main body 6a. For example, the attachment portion 664 includes a pair of engagement portions 664a, a pair of resiliently deformable portions 664b, and a pair of grab portions 664c.

The stopper 6b includes the attachment portion 664 provided on the stopper body 64, wherein the attachment portion 664 of the stopper body 64 is configured to detachably attach the stopper body 64 to the adaptor main body 6a. The stopper 6b is configured such that the rotation restriction portions 65 of the stopper body 64 restrict the rotations of the drive transmission members 61 in a state where the stopper body 64 is attached to the adaptor main body 6a with the attachment portion 664 of the stopper body 64. Thus, after the adaptor main body 6a is attached to the drive parts 21b of the robot arm 21, the stopper 6b can be detached from the adaptor main body 6a at the attachment portion 664. Accordingly, upon attaching the surgical instrument 4 to the drive parts 21b via the adaptor main body 6a, the stopper 6b can be detached from the adaptor main body 6a. Thus, the adaptor main body 6a itself does not need to have a structure for restricting the rotations of the drive transmission members 61. Therefore, without providing an extra internal structure and/or an extra internal space in the adaptor main body 6a of the adaptor 6, the rotations of the drive transmission members 61 can be restricted by the rotation restriction portions 65 of the stopper 6b of the adaptor 6. As a result, the rotations of the drive transmission members 61 due to the rotations of the drive parts 21b can be prevented, while preventing a complicated and enlarged structure of the adaptor main body 6a.

The attachment portion 664 is configured to restrict the movements of the stopper body 64 relative to the adaptor main body 6a (see FIG. 4) in a state where the adaptor main body 6a is attached to the stopper body 64.

Figure 13:
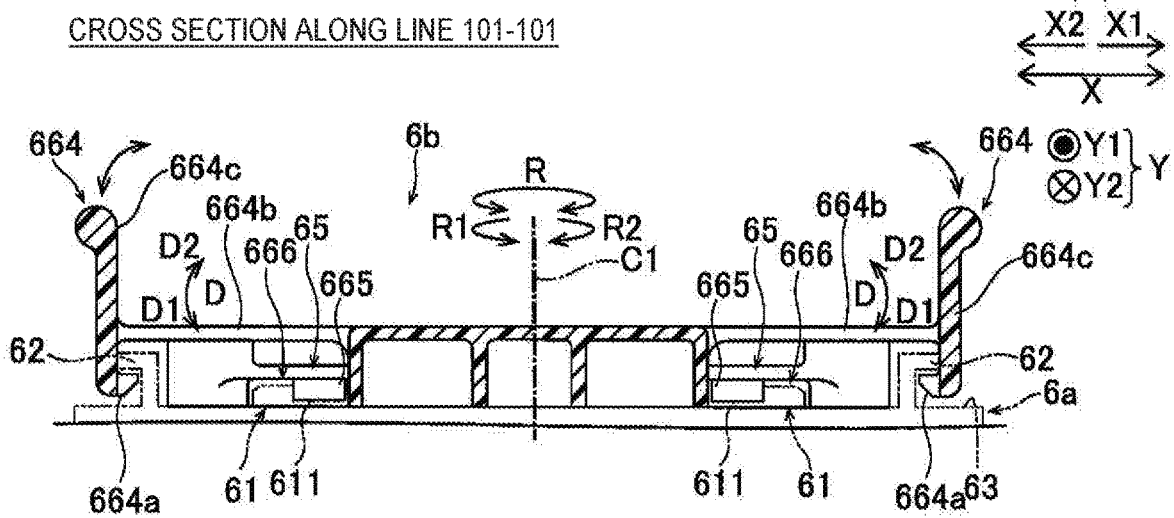
FIG. 13 is a diagram illustrating a sectional view taken along line 101-101 of FIG. 12.

Specifically, as illustrated in FIGS. 12 and 13, the attachment portion 664 includes the pair of engagement portions 664a that is detachably engaged with the adaptor main body 6a and restrict the movements of the stopper body 64 relative to the adaptor main body 6a. Because the pair of engagement portions 664a restricts the movements of the stopper body 64 relative to the adaptor main body 6a, the movement (co-rotation) of the stopper body 64 due to the rotations of the drive transmission members 61 can be prevented by the pair of engagement portions 664a As a result, the rotations of the drive transmission members 61 of the adaptor main body 6a are more easily restricted by the rotation restriction portions 65. Further, by simply providing the pair of engagement portions 664a on the stopper body 64, the stopper 6b can be detachably attached to the adaptor main body 6a. Thus, the structure of the stopper body 64 for detachably attaching the stopper 6b to the adaptor main body 6a can be simplified. The stopper body 64 is attached to the adaptor main body 6a such that the stopper body 64 is engaged with symmetrical positions in the adaptor main body 6a by the pair of engagement portions 664a. As a result, after attaching the stopper body 64 to the adaptor main body 6a, it is possible to suppress displacement of the stopper body 64 with respect to the adaptor main body 6a.

The pair of engagement portions 664a is configured to restrict the movement of the stopper body 64 in the Z direction and the rotations of the stopper body 64 about the center axis C1 of the stopper body 64 parallel to the Z direction. Here, in the direction (X direction) in which the grab portions 664c face each other, the engagement portions 664a are respectively projected toward the center axis C1 from the inner surfaces of the pair of grab portions 664c on the center axis C1 side. In the direction (the Z direction) in which the adaptor main body 6a and the stopper 6b are adjacent to each other, the engagement portions 664a are formed at end portions of the grab portions 664c on the side of the adaptor main body 6a, respectively. Each engagement portion 664a includes plural (two) portions in the direction (Y direction) in which the surgical instrument 4 extends. Such a pair of engagement portions 664a contacts with the movement restriction surface of the adaptor main body 6a from the Z2 side and thereby restricts the movement of the stopper body 64 in the Z direction.

Specifically, the pair of engagement portions 664a is detachably engaged with the pair of guide rails 62 (see FIG. 4) provided at the adaptor main body 6a, wherein the pair of guide rails 62 is configured to guide attaching of the surgical instrument 4 to the adaptor main body 6a. Accordingly, the adaptor main body 6a does not need to have a structure for attaching the stopper 6b to the adaptor main body 6a in addition to the pair of guide rails 62 to attach the surgical instrument 4 to the adaptor main body 6a. This can prevent the adaptor main body 6a from having a complicated and enlarged structure.

The movements of the stopper body 64 in the Z direction are restricted by contacting, in the Z direction, the Z1 side portions of the engagement portions 664a with the portions of the guide rails 62 facing the engagement portions 664a. The rotations of the stopper body 64 about the center axis C1 restricted by contacting, in the X direction, the C1 side portions of the engagement portions 664a with the portions of the guide rails 62 on the opposite side of the center axis C1

Each of the pair of resiliently deformable portions 664b is configured to be resiliently deformed along with movements of the pair of grab portions 664c. Here, in the direction (the X direction) in which the grab portions 664c are opposed to each other, the pair of resiliently deformable portions 664b connects the pair of grab portions 664c with the stopper body 64. Each of the resiliently deformable portions 664b is formed in a thin plate shape in the direction (the Z direction) in which the adaptor main body 6a and the stopper 6b are adjacent to each other. Each of the resiliently deformable portions 664b is resiliently deformable in the circumferential direction D (see FIG. 13) about the center axis C2 (see FIG. 14) of the stopper body 64 parallel to the longitudinal direction (the Y direction) of the surgical instrument 4, toward the direction D1 which is one side of the circumferential direction D and toward the direction D2 which is the other side of the circumferential direction D. The thickness of each of the resiliently deformable portions 664b is less than the thickness of each of the grab portions 664c.

The attachment portion 664 of the stopper body 64 is configured, when the stopper body 64 is moved to the adaptor main body 6a along the direction (the Z direction) orthogonal to the Z1 side surface 63 of the adaptor main body 6a, to attach the stopper body 64 to the adaptor main body 6a, and is configured, when the stopper body 64 is moved away from the adaptor main body 6a in the Z direction, to detach the stopper body 64 from the adaptor main body 6a.

Specifically, the attachment portion 664 includes the pair of grab portions 664c, wherein the pair of grab portions 664c is configured to move the pair of engagement portions 664a in the direction D2 away from the adaptor main body 6a or the direction D1 closer to the adaptor main body 6a while elastically deforming a part of the stopper body 64. With this configuration, the stopper body 64 can be attached to and detached from the adaptor main body 6a by means of the pair of engagement portions 664a by only operating the pair of grab portions 664c to elastically deform the part of the stopper body 64. This facilitates the operation of attaching or detaching the stopper 6b to or from the adaptor main body 6a.

That is, by the movement of the pair of engagement portions 664a along with the movement of the pair of grab portions 664c, the attachment state of the stopper 6b and the detachment state of the stopper 6b are switched. Specifically, the stopper 6b is detached from the adaptor main body 6a, by resiliently deforming the pair of resiliently deformable portions 664b toward the center axis C1 along the circumferential direction D (see FIG. 13) about the center axis C2 (see FIG. 14) of the stopper body 64 parallel to the longitudinal direction of the surgical instrument 4. To the contrary, the stopper 6b is attached to the adaptor main body 6a from the detached state, by resiliently deforming the pair of resiliently deformable portions 664b away from the center axis C1 along the circumferential direction D (see FIG. 13) about the center axis C2 (see FIG. 14) of the stopper body 64 parallel to the longitudinal direction of the surgical instrument 4. In the attached state of the stopper 6b, the pair of guide rails 62 of the adaptor main body 6a is sandwiched between the pair of engagement portions 664a of the attachment portion 664 in the X direction.

(Rotation Restriction Portion)

Figure 14:
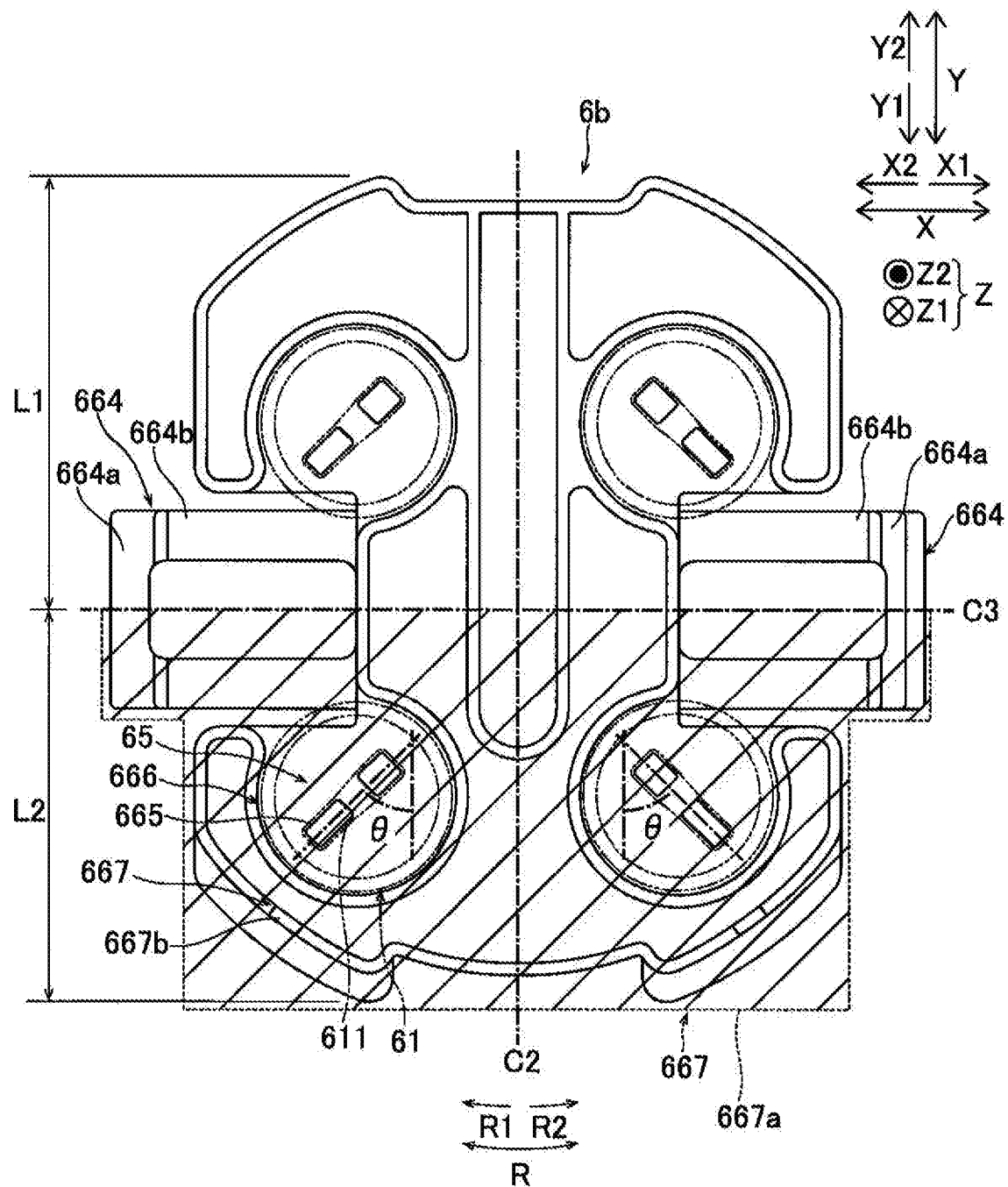
FIG. 14 is a diagram illustrating a plan view of the stopper according to a first embodiment as viewed from the Z2 side.

As illustrated in FIGS. 13 and 14, each of the rotation restriction portions 65 is provided being inclined by a predetermined angle $\theta$ in the circumferential direction R about the rotational axis C1 of the corresponding drive transmission member 61 with respect to the center axis C2 of the stopper body 64 parallel to the longitudinal direction (the Y direction) of the surgical instrument 4. With this, the drive transmission member 61 can be fixed to a second position being displaced by the predetermined angle $\theta$ from a first position (engagement position) of the drive transmission member 61 for engaging the adaptor main body 6a and the surgical instrument 4 with each other. Accordingly, the drive transmission member 61 can be rotated by a sufficient rotational angle to engage the adaptor main body 6a with the surgical instrument 4. This can prevent insufficient rotations of the drive transmission members 61 upon engaging the adaptor main body 6a with the surgical instrument 4, to thereby preventing an insufficient engagement between the adaptor main body 6a and the surgical instrument 4. As a result, the surgical instrument 4 can be securely attached to the adaptor main body 6a.

Note that one side along the circumferential direction R is referred to as a first circumferential direction R1 and the other side along the circumferential direction R is referred to as a second circumferential direction R2.

Specifically, the rotation restriction portion 65 is configured to fix an initial position (initial state) of the engagement recess 611 of the drive transmission member 61 in the adaptor main body 6a to a position inclined by the predetermined angle $\theta$, to prevent the engagement projection 441 (see FIG. 5) of the surgical instrument 4 from being placed on the edge of the engagement recess 611 of the drive transmission member 61 of the adaptor main body 6a upon attaching the surgical instrument 4 to the adaptor main body 6a. Note that the initial state refers to a state at the start of the operation of engaging the engagement projection 441 of the surgical instrument 4 with the corresponding engagement recess 611 of the adaptor main body 6a upon attaching the surgical instrument 4 to the adaptor main body 6a.

The predetermined angle $\theta$ is an angle by which the engagement projection 441 (see FIG. 5) of the driven member 44 of the surgical instrument 4 is not completely engaged with the engagement recess 611 of the corresponding drive transmission member 61 of the adaptor main body 6a in the initial state. For example, the predetermined angle $\theta$ may be 5 degrees or more and 80 degrees or less in either the first circumferential direction R1 or the second circumferential direction R2 with respect to the center axis C2. Note that it may be preferable that the predetermined angle $\theta$ is inclined with respect to the center axis C2 at approximately 45 degrees to either the first circumferential direction R1 or the second circumferential direction R2, from the viewpoint of the time required to engage the engagement projection 441 of the surgical instrument 4 with the engagement recess 611 of the adaptor main body 6a and the assuredness of the engagement between the engagement projection 441 of the surgical instrument 4 and the engagement recess 611 of the adaptor main body 6a.

The rotation restriction portion 65 is configured to be in contact with an inside surface of the engagement recess 611 of the adaptor main body 6a, to thereby restricting the rotations of the drive transmission member 61 with the drive transmission member 61 being inclined to either the first circumferential direction R1 or the second circumferential direction R2 about the center axis C1 of the stopper body 64 with respect to the center axis C2 by the predetermined angle θ.

Specifically, the rotation restriction portion 65 of the stopper 6b includes fitting projections 665. Each of the fitting projections 665 is fitted to the corresponding engagement recess 611 of the adaptor main body 6a, which is recessed from the surgical instrument 4 side surface of the drive transmission member 61 in the direction away from the surgical instrument 4. The fitting projection 665 is provided at the stopper body 64 with the fitting projection 665 being inclined by the predetermined angle θ. With this configuration, by fitting the fitting projection 665 of the stopper body 64 into the engagement recess 611 of the drive transmission member 61 in the adaptor main body 6a, the rotations of the drive transmission member 61 are restricted with the drive transmission member 61 inclined by the predetermined angle θ. Thus, the rotations of the drive transmission member 61 can be restricted without an additional structure therefor in the adaptor main body 6a. This can further facilitate the prevention of the complicated and enlarged structure of the adaptor main body 6a.

The fitting projection 665 is provided at the Z2 side surface of the stopper body 64. The fitting projection 665 has a block shape (substantially rectangular parallelepiped shape). The fitting projection 665 is projected from the Z2 side surface of the stopper body 64 toward the Z2 direction. The fitting projection 665 has a projecting length (height) accommodated within the thickness of the stopper body 64. The fitting projection 665 is divided into plural pieces (two pieces) in the direction inclined by the predetermined angle θ with respect to the center axis C2.

The fitting projection 665 extends in the direction inclined by the predetermined angle θ to either the first circumferential direction R1 or the second circumferential direction R2 with respect to the center axis C2. That is, the fitting projection 665 is relatively inclined by the predetermined angle θ to either the first circumferential direction R1 or the second circumferential direction R2 with respect to the engagement recess 611 of the adaptor main body 6a.

By manually rotating the drive transmission member 61 (the engagement recess 611) of the adaptor main body 6a by the worker, the fitting projection 665 of the stopper 6b gets fitted to the engagement recess 611 of the drive transmission member 61 of the adaptor main body 6a. Here, the fitting projection 665 is fitted to the engagement recess 611 of the adaptor main body 6a with a small gap therebetween (i.e., a loose fit state).

In the state where the fitting projection 665 of the stopper 6b and the engagement recess 611 of the adaptor main body 6a are fitted to each other, the fitting projection 665 is in contact with the inner surface of the engagement recess 611 of the adaptor main body 6a, to thereby restricting the rotations of the engagement recess 611 of the adaptor main body 6a due to the rotations of the engagement projection 211 of the drive part 21b. Further, in the state where the fitting projection 665 of the stopper 6b and the engagement recess 611 of the adaptor main body 6a are fitted to each other, the fitting projection 665 is in contact with the inner surface of the engagement recess 611 of the adaptor main body 6a, to thereby restricting relative movements of the stopper body 64 with respect to the adaptor main body 6a in the X direction and the Y direction.

The fitting projection 665 includes plural (four) fitting projections 665. With this, even if the plural engagement recesses 611 are respectively provided to the plural drive transmission members 61 of the adaptor main body 6a, the rotations of the plural drive transmission members 61 can be restricted by the plural fitting projections 665 of the stopper body 64, without providing an additional configuration therefor to the adaptor main body 6a. This can further facilitate the prevention of the complicated and enlarged structure of the adaptor main body 6a.

The fitting projections 665 are provided on a surface of the stopper body 64 opposed to the surgical instrument 4 side surface 63 of the adaptor main body 6a. Each of the fitting projections 665 is located at the position where the fitting projection 665 can be surely fitted to the corresponding engagement recesses 611 of the adaptor main body 6a by manually rotating the engagement recesses 611 of the adaptor main body 6a by the worker.

The plural fitting projections 665 are arranged to be line-symmetric with respect to the center axis C2 of the stopper body 64 parallel to the longitudinal direction of the surgical instrument 4. Accordingly, by rotating the drive transmission members 61 in the opposite directions with respect to the center axis C2 of the stopper body 64, the engagement recesses 611 can be engaged with the fitting projections 665, respectively. Therefore, the work of attaching the stopper 6b to the adaptor main body 6a can be easily performed.

For example, among all the fitting projections 665 in the stopper body 64, the number of the fitting projections 665 provided on the X1 side of the center axis C2 of the stopper body 64 and the number of the fitting projections 665 provided on the X2 side of the center axis C2 of the stopper body 64 are the same (two). Two of the fitting projections 665 are provided on the X1 side of the center axis C2 of the stopper body 64 and arranged side by side in the Y direction while being inclined with respect to the center axis C2 toward the second circumferential direction R2 by the predetermined angle θ. To the contrary, the other two of the fitting projections 665 are provided on the X2 side of the center axis C2 of the stopper body 64 and arranged side by side in the Y direction while being inclined with respect to the center axis C2 toward the first circumferential direction R1 by the predetermined angle θ.

(Restriction Portion Recess)

The rotation restriction portion 65 is configured to suppress the thickness, in the Z direction, of portions of the stopper body 64 in the vicinity of the fitting projections 665.

Specifically, the rotation restriction portion 65 includes a restriction portion recess 666 provided around the fitting projection 665 and recessed toward the direction (the Z1 direction) away from the adaptor 6. The restriction portion recess 666 is configured such that the outer circumferential portion of the drive transmission member 61 is inserted into the restriction portion recess 666. With this configuration, the thickness of the portions of the stopper body 64 in the vicinity of the fitting projections 665 can be reduced. Thus, a shrinkage of the stopper body 64 that may occur when the stopper body 64 is manufactured can be reduced. As a result, the occurrence of biased stress in the stopper body 64 can be further suppressed. Further, the thickness, in the Z direction, of the stopper body 64 can be reduced and the fitting projections 665 can be fully inserted into the engagement recesses 611 of the adaptor main body 6a.

Specifically, by inserting the fitting projection 665 into the engagement recess 611 of the adaptor main body 6a up to the base portion of the fitting projection 665 on the Z1 side in the state where the fitting projection 665 of the stopper 6b and the engagement recess 611 of the adaptor main body 6a are fitted to each other, the outer circumferential portion of the drive transmission member 61 is inserted into the restriction portion recess 666. The restriction portion recess 666 is recessed from the Z2 side surface of the stopper body 64 toward the Z1 side along the Z direction. In the Z direction, the length of the restriction portion recess 666 is larger than the projecting length of the fitting projection 665. In the Z direction, the length of the restriction portion recess 666 is smaller than the maximum thickness of the stopper body 64.

As viewed from the Z2 side, the shape of the restriction portion recess 666 corresponds to the shape of the drive transmission member 61. Here, as viewed from the Z2 side, the inner diameter of the restriction portion recess 666 is larger than the drive transmission member 61.

(Discrimination Portion)

The stopper body 64 is configured such that the worker can recognize the correct orientation of the stopper 6b with respect to the adaptor main body 6a, upon attaching the stopper 6b to the adaptor main body 6a.

Specifically, the stopper body 64 includes a discrimination portion 667 to indicate the orientation of the stopper 6b with respect to the longitudinal direction of the surgical instrument 4 upon attaching the stopper 6b to the adaptor main body 6a (see FIG. 4). Accordingly, the worker can attach the stopper 6b in the correct orientation thereof to the adaptor main body 6a, and this can improve the workability of attaching the stopper 6b to the adaptor main body 6a.

The discrimination portion 667 includes a first discrimination portion 667a and a second discrimination portion 667b.

The first discrimination portion 667a is configured such that one side of the stopper body 64 is smaller than the other side of the stopper body 64 in the longitudinal direction of the surgical instrument 4 (the Y direction). That is, the first discrimination portion 667a is configured such that a length L2 (see FIG. 14) of a portion of the stopper body 64 on the Y1 side with respect to the center line C3 of the grab portions 664c extending in the X direction is smaller than a length L1 (see FIG. 14) of a portion of the stopper body 64 on the Y2 side with respect to the center line C3.

The second discrimination portion 667b is configured to have a recess 667c or a cutout at only one side, in the longitudinal direction of the surgical instrument 4 (the Y direction), of a rim (or an edge) of the stopper body 64. That is, the second discrimination portion 667b is configured to have the recess 667c such that the recess 667c (cutout) is formed at the rim or the edge of the stopper body 64 only on the Y1 side with respect to the center line C3 of the grab portions 664c, but not formed on the Y2 side with respect to the center line C3, in the longitudinal direction of the surgical instrument 4 (the Y direction). Here, the recess 667c is recessed from the end of the rim of the stopper body 64 on the Z2 side toward the Z1 side.

(Method of Assembling Adaptor)

Figure 16:
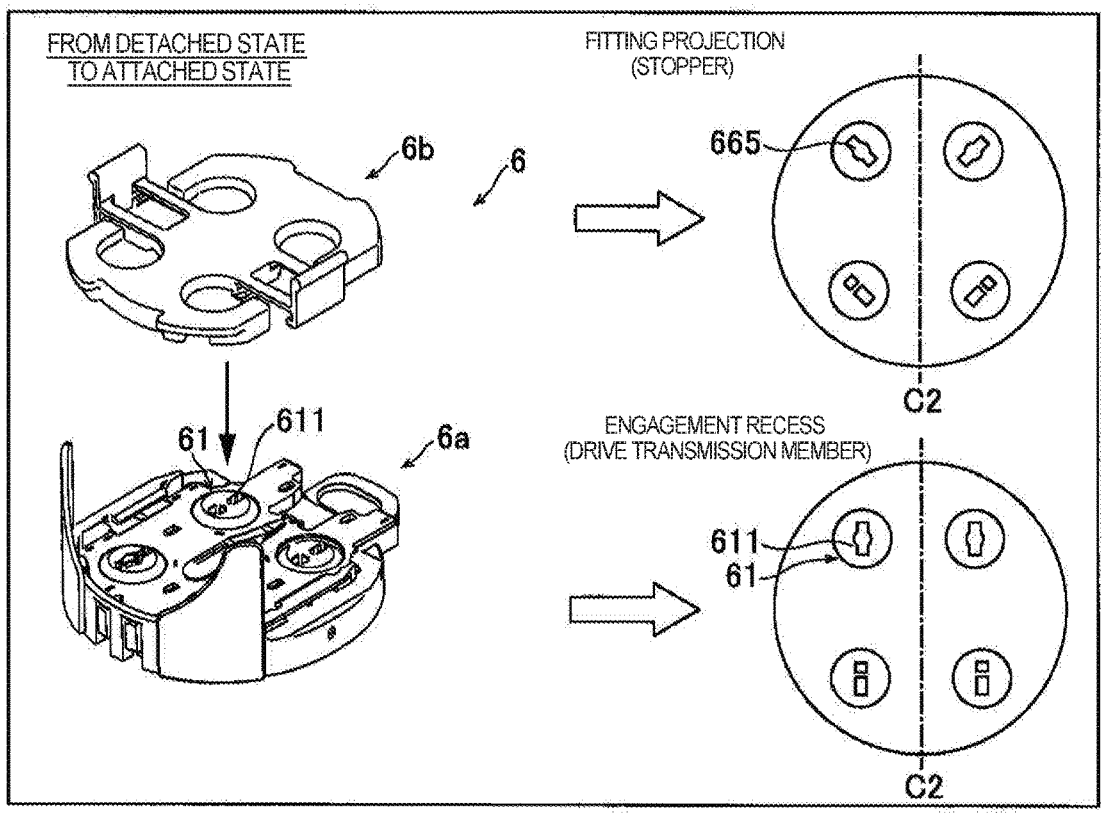
FIG. 16 is diagram illustrating a schematic view of a state when the stopper is attached to the drive transmission members according to a first embodiment.
Figure 17:
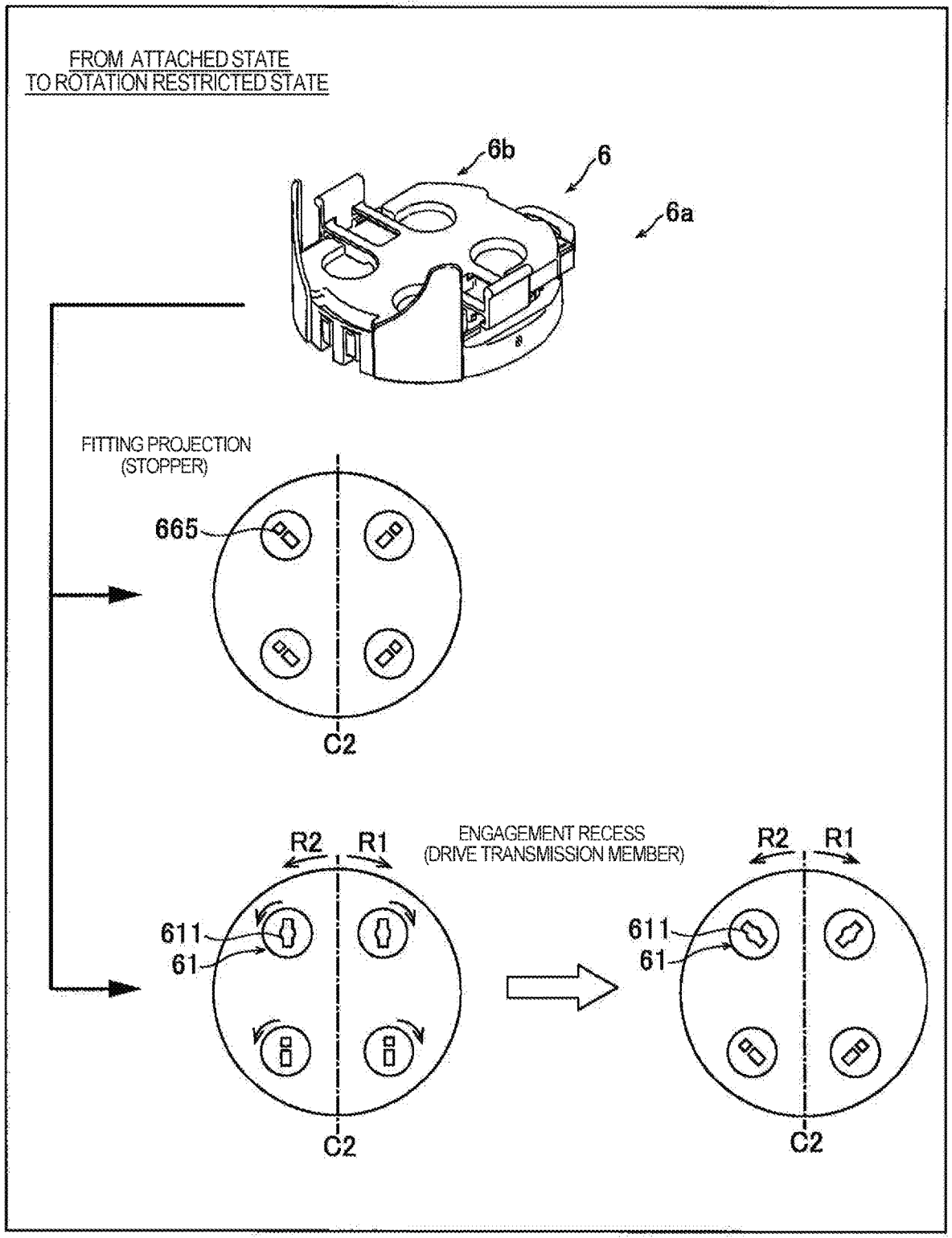
FIG. 17 is a diagram illustrating a schematic view of a state in which rotations of the drive transmission members are restricted by the stopper according to a first embodiment.

Hereinafter, with reference to FIGS. 15 to 17, a method of assembling the adaptor 6 including the adaptor main body 6a and the stopper 6b. By this assembling method, the adaptor 6 is prepared which is capable of retaining a state in which the inclination angles of the engagement recesses 611 of the adaptor main body 6a are fixed at the predetermined angle θ. Note that in FIGS. 16 and 17, the center axis C2 of the stopper body 64 is illustrated on the adaptor main body 6a and the first circumferential direction R1 and the second circumferential direction R2 are illustrated on the adaptor main body 6a, to facilitate understanding.

Figure 15:
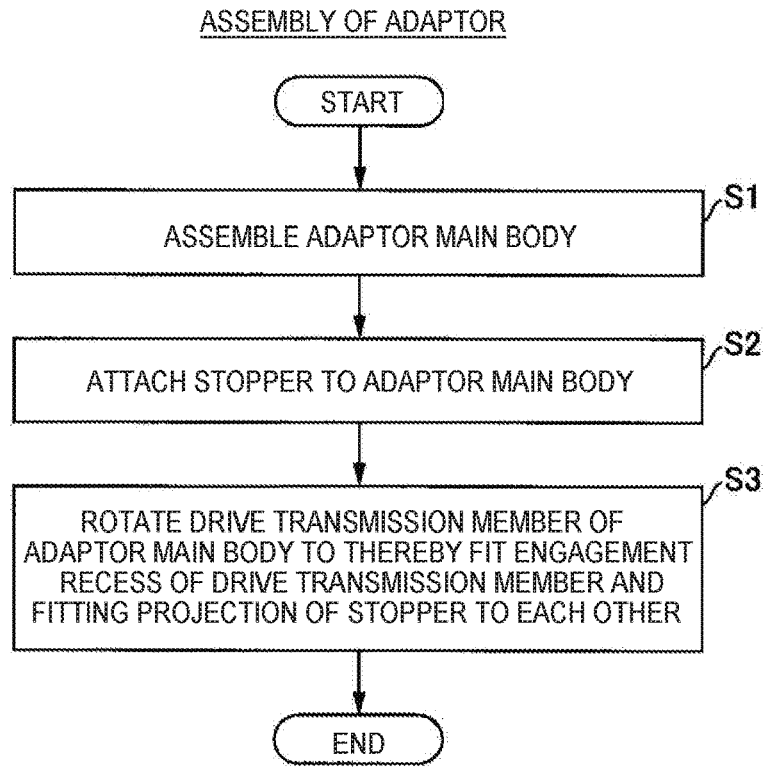
FIG. 15 is a flowchart illustrating a method of assembling the adaptor using the stopper according to a first embodiment.

As illustrated in FIG. 15, in Step S1, the worker assembles the adaptor main body 6a.

In Step S2, the worker attaches the stopper 6b to the adaptor main body 6a. Specifically, as illustrated in FIG. 16, the worker puts the detached stopper 6b closer to the adaptor main body 6a, and attaches the stopper 6b to the adaptor main body 6a in a state where the fitting projections 665 of the stopper 6b and the drive transmission members 61 of the adaptor main body 6a are in contact with each other. As a result, the pair of engagement portions 664a of the stopper 6b and the pair of guide rails 62 of the adaptor main body 6a are respectively engaged with each other. In this state, the fitting projections 665 of the stopper 6b are inclined with respect to the direction of the center axis C2 by the predetermined angle θ, while the engagement recesses 611 of the adaptor main body 6a are substantially parallel to the direction of the center axis C2. Note that, in this state, it is not limited to the case where the engagement recesses 611 of the adaptor main body 6a are substantially parallel to the direction of the center axis C2, but the engagement recesses 611 of the adaptor main body 6a may be inclined with respect to the direction of the center axis C2 by an angle(s) different from the predetermined angle θ, for example.

As illustrated in FIG. 15, in Step S3, the worker rotates the drive transmission members 61 of the adaptor main body 6a to thereby fitting the engagement recesses 611 of the adaptor main body 6a and the fitting projections 665 of the stopper 6b to each other. Specifically, as illustrated in FIG. 17, the worker rotates the drive transmission members 61 of the adaptor main body 6a manually (for example, operating directly by hand or using a tool) in the state where the stopper 6b is attached to the adaptor main body 6a, to thereby fit the engagement recesses 611 of the adaptor main body 6a and the fitting projections 665 of the stopper 6b to each other. At this time, the worker rotates, in the first circumferential direction R1, the engagement recesses 611 provided on one side from the center axis C2 among all the engagement recesses 611 of the adaptor main body 6a, whereas the worker rotates, in the second circumferential direction R2, the engagement recesses 611 provided on the other side from the center axis C2 among all the engagement recesses 611 of the adaptor main body 6a.

With this operation, the adaptor 6 in the rotation restricted state where the rotational positions (rotational angles) of the engagement recesses 611 of the adaptor main body 6a are fixed at the predetermined angle θ is manufactured. Then, the operation of assembling the adaptor 6 by the worker is ended. Note that a package in which the adaptor 6 and the drape 7 (see FIG. 4) are packed together is shipped as a product.

(Method of Attaching Surgical Instrument to Robot Arm)

Figure 18:
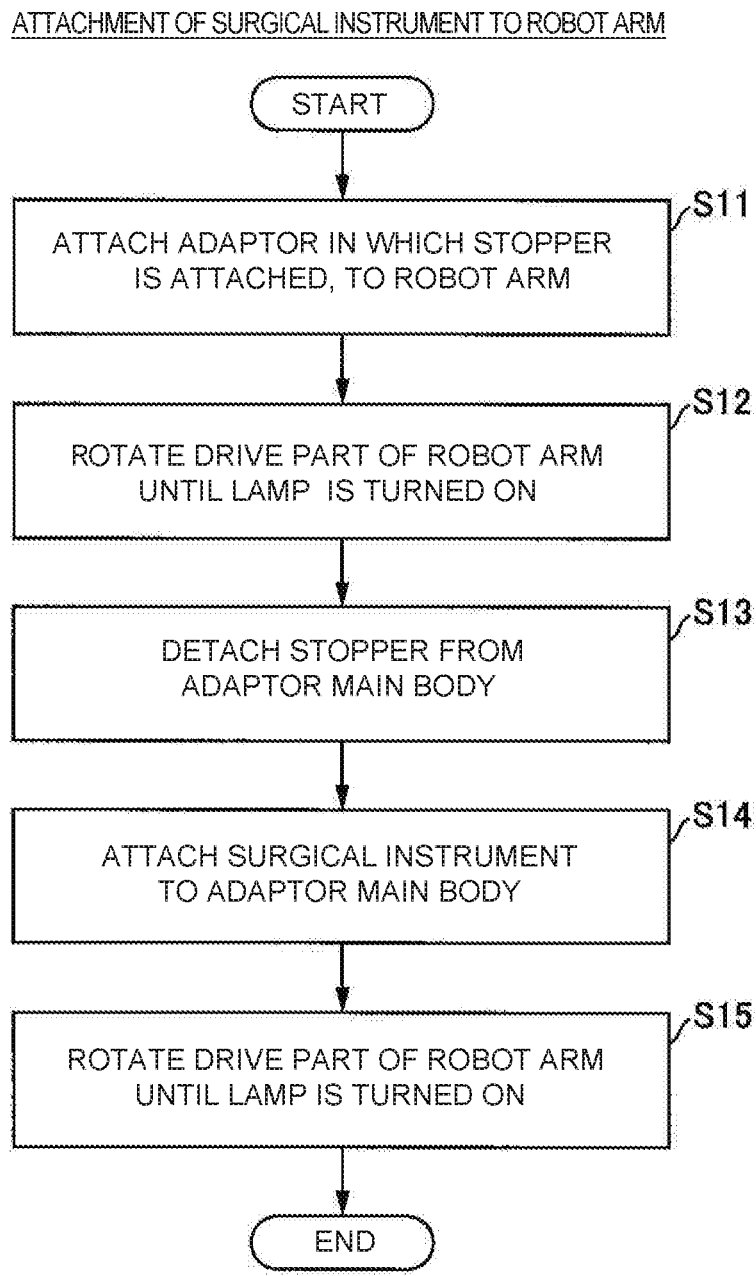
FIG. 18 is a flowchart illustrating a method for attaching the surgical instrument to the robot arm using the stopper according to a first embodiment.
Figure 19:
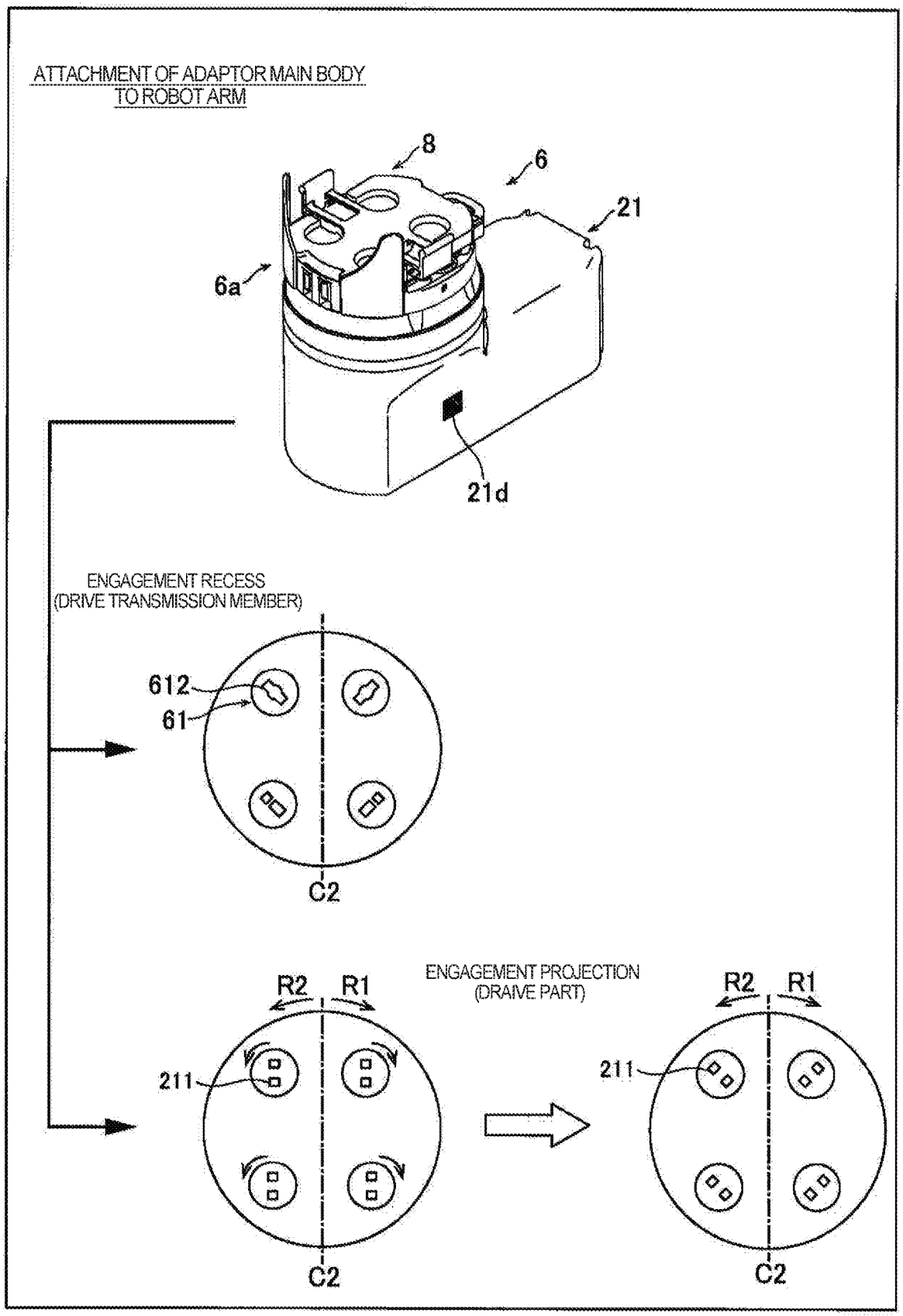
FIG. 19 is a diagram illustrating a schematic view of a state when the adaptor main body is attached to the robot arm according to a first embodiment.
Figure 20:
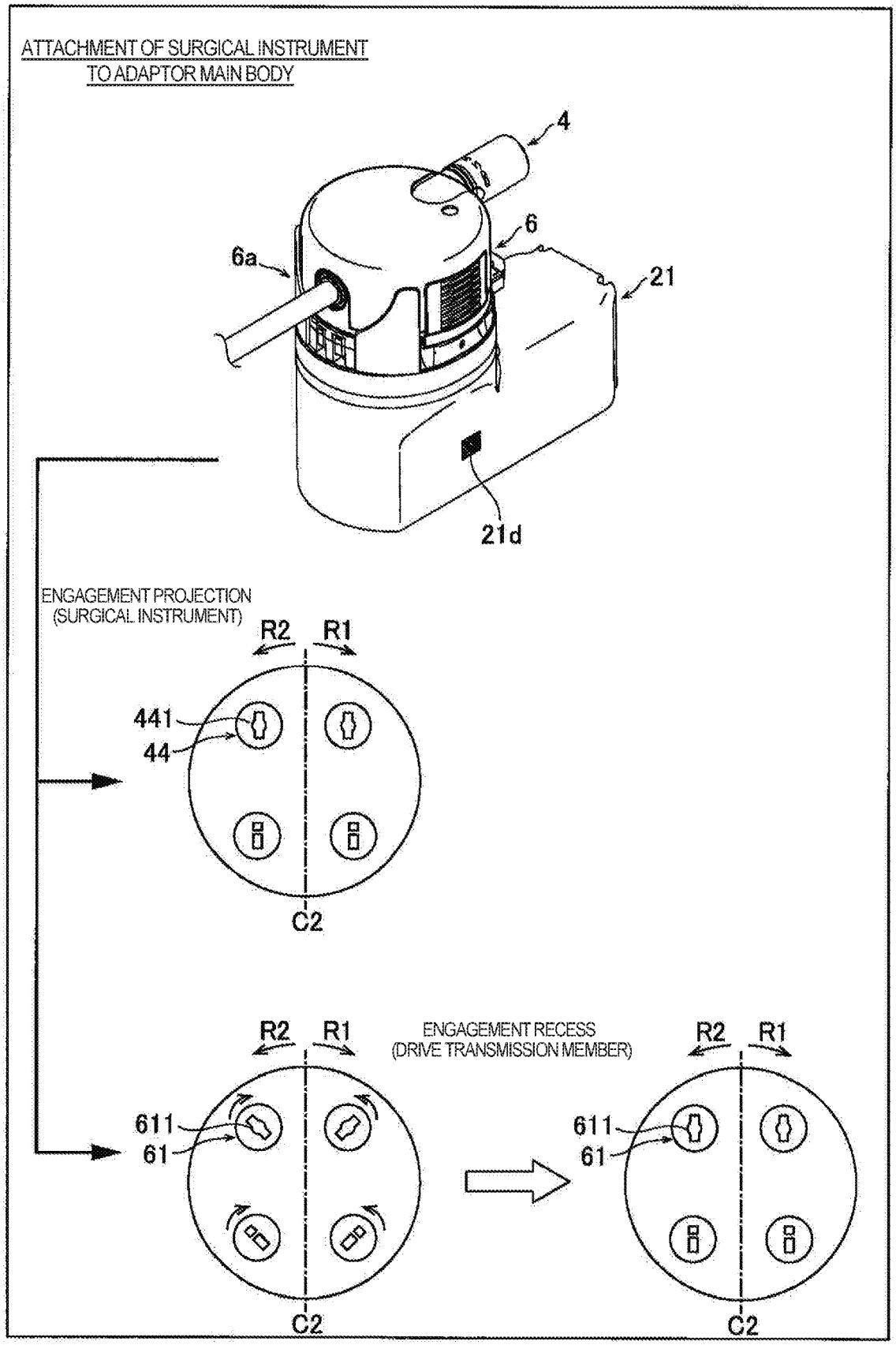
FIG. 20 is a diagram illustrating a schematic view of a state when the surgical instrument is attached to the adaptor main body according to a first embodiment.

With reference to FIGS. 18 to 20, a method of attaching the surgical instrument 4 to the robot arm 21 via the adaptor main body 6a is described below. Note that the process of attaching the surgical instrument 4 to the robot arm 21 via the adaptor main body 6a may be executed by an assistant Sp (see FIG. 1) as a worker. In FIGS. 19 and 20, the center axis C2 is also illustrated to the adaptor main body 6a and the drive parts 21b and a first circumferential direction R1 and a second circumferential direction R2 are also illustrated to the adaptor main body 6a and the surgical instrument 4 to facilitate understanding.

As illustrated in FIG. 18, in Step S11, the worker attaches, to the robot arm 21, the adaptor 6 in which the stopper 6b is already attached. At this time, the engagement recesses 612 (see FIG. 6) of the drive transmission members 61 and the engagement projections 211 of the robot arm 21 have not been fitted to each other yet.

In step S12, the worker has the drive parts 21b of the robot arm 21 rotate until the lamp 21d is turned on. Specifically, as illustrated in FIG. 19, the worker operates to drive or the controller 141 automatically drives the drive parts 21b of the robot arm 21, to thereby fit the engagement projections 211 of the robot arm 21 to the engagement recesses 612 of the drive transmission members 61 by the driving of the drive parts 21b of the robot arm 21. The fitting between the engagement projections 211 of the robot arm 21 and the engagement recesses 612 of the drive transmission members 61 is detected by the detection result by the encoder 215. For example, when the rotational speed of the engagement projections 211 of the robot arm 21 gets smaller than a predetermined speed, the encoder 215 detects that the fitting between the engagement projections 211 of the robot arm 21 and the engagement recesses 612 of the drive transmission members 61. At this time, the lamp 21d of the robot arm 21 is turned on to inform the worker of the completion of the fitting between the engagement projections 211 of the robot arm 21 and the engagement recesses 612 of the drive transmission members 61. When the completion of the fitting between the engagement projections 211 of the robot arm 21 and the engagement recesses 612 of the drive transmission members 61 is detected, the controller 141 stops the rotations of the engagement projections 211 of the drive parts 21b of the robot arm 21.

In this operation, the stopper 6b is attached to the adaptor main body 6a, and thus the drive transmission members 61 cannot be rotated with the rotations of the drive parts 21b. That is, the rotations of the drive transmission members 61 due to the rotations of the drive parts 21b are prevented.

As illustrated in FIG. 18, in Step S13, the worker detaches the stopper 6b from the adaptor main body 6a. In Step S14, the worker attaches the surgical instrument 4 to the adaptor main body 6a. At this time, the engagement recesses 611 of the adaptor main body 6a and the engagement projections 441 of the surgical instrument 4 have not been engaged yet.

In Step S15, the worker has the drive parts 21b of the robot arm 21 rotate until the lamp 21d is turned on. Specifically, as illustrated in FIG. 20, the worker operates to drive or the controller 141 automatically drives the drive parts 21b of the robot arm 21, to thereby fit the engagement projections 441 of the surgical instrument 4 to the engagement recesses 611 of the adaptor main body 6a by the driving of the drive parts 21b of the robot arm 21. The fitting between the engagement projections 441 of the surgical instrument 4 and the engagement recesses 611 of the adaptor main body 6a is detected by the detection result by the optical sensor 21c. For example, when the light emitted from the light emission part 221 of the optical sensor 21c is not blocked by the light blocking part 213a of the drive part 21b, the optical sensor 21c detects that the engagement projections 441 of the surgical instrument 4 and the engagement recesses 611 of the adaptor main body 6a are engaged with each other. At this time, the lamp 21d of the robot arm 21 is turn on to inform the worker of the completion of the engagement between the engagement projections 441 of the surgical instrument 4 and the engagement recesses 611 of the adaptor main body 6a. Note that the sensor that detect the fitting state is not limited to an optical sensor, and thus may be any sensor that can detect a change in the height of the detection member 213 due to the change of the fitting state, such as a magnetic sensor, for example.

With this operation, the surgical instrument 4 is attached (fixed) to the robot arm 21 via the adaptor main body 6a. Thus, the operation of attaching the surgical instrument 4 to the robot arm 21 by the worker is completed.

Note that every time the surgical instrument 4 is replaced, the operation of attaching the surgical instrument 4 to the robot arm 21 is executed. Every time the surgical instrument 4 is replaced, the used adaptor 6 may be discarded and a new adaptor 6 may be used. Every time the surgical instrument 4 is replaced, the adaptor main body 6a of the used adaptor 6 may be discarded and the stopper 6b of the used adaptor 6 may be reused and attached to a new adaptor main body 6a.

Second Embodiment

With reference to FIGS. 21 to 40, a stopper 806b according to a second embodiment is described. Different from the adaptor 6 including the stopper 6b according to a first embodiment, an adaptor 806 according to a second embodiment includes the stopper 806b including rotation restriction portions 8163 which are capable of being deformed in the direction of a rotational axis B of drive transmission members 861. In the drawings, the constituents same as in a first embodiment are designated by the same reference numerals.

Figure 21:
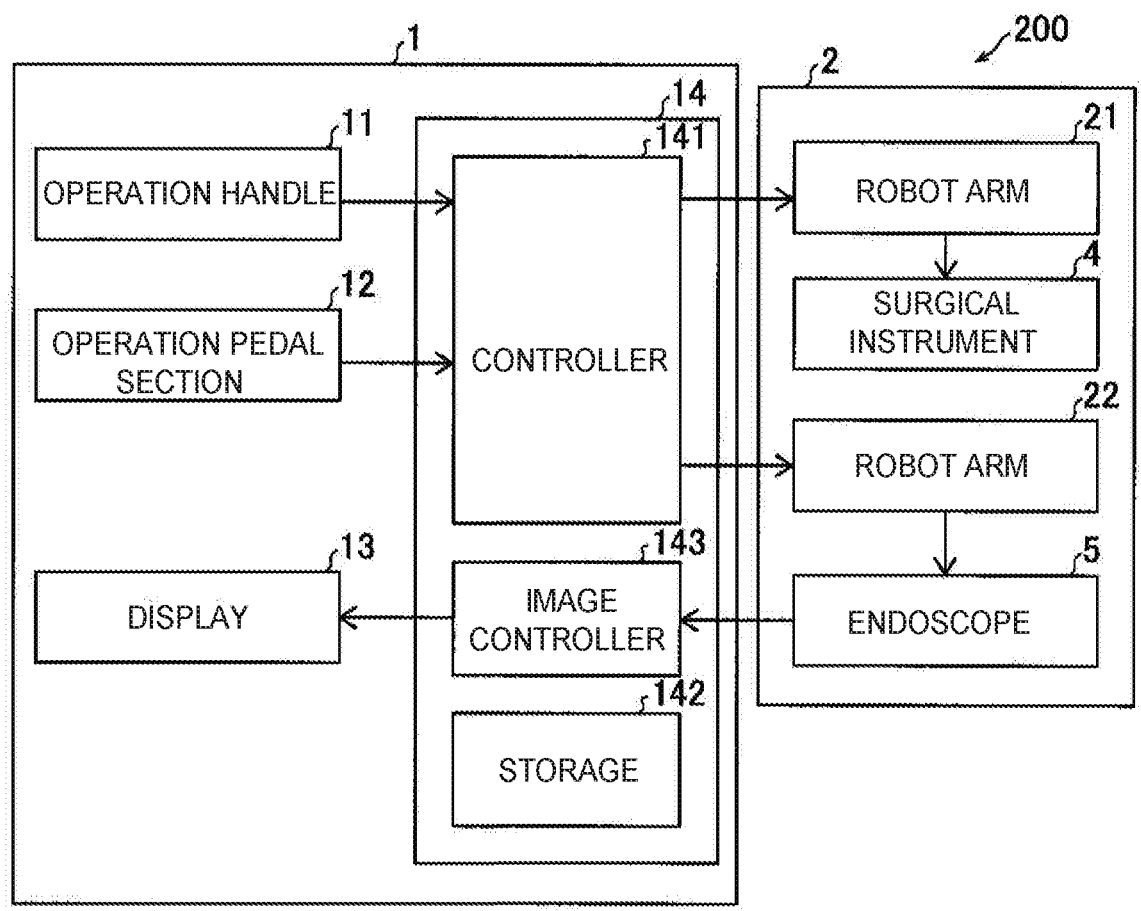
FIG. 21 is a block diagram illustrating a view of a control-related configuration of a robot surgery system according to a second embodiment.

As illustrated in FIG. 21, a robotic surgical system 200 according to a second embodiment includes the remote control apparatus 1 and the patient-side apparatus 2. The remote control apparatus 1 includes the operation handles 11, the operation pedal section 12, the display part 13, and the control apparatus 14. The patient-side apparatus 2 includes the surgical instruments 4, the endoscope 5, the robot arms 21, and the robot arm 22.

(Configuration of Surgical Instrument, Adaptor, Drape, and Robot Arm)

With reference to FIGS. 22 to 38, the configurations of the surgical instrument 4 including driven members 4a, an adaptor 806 including an adaptor main body 806a, the drape 7, and the robot arm 21 are described below.

Figure 22:
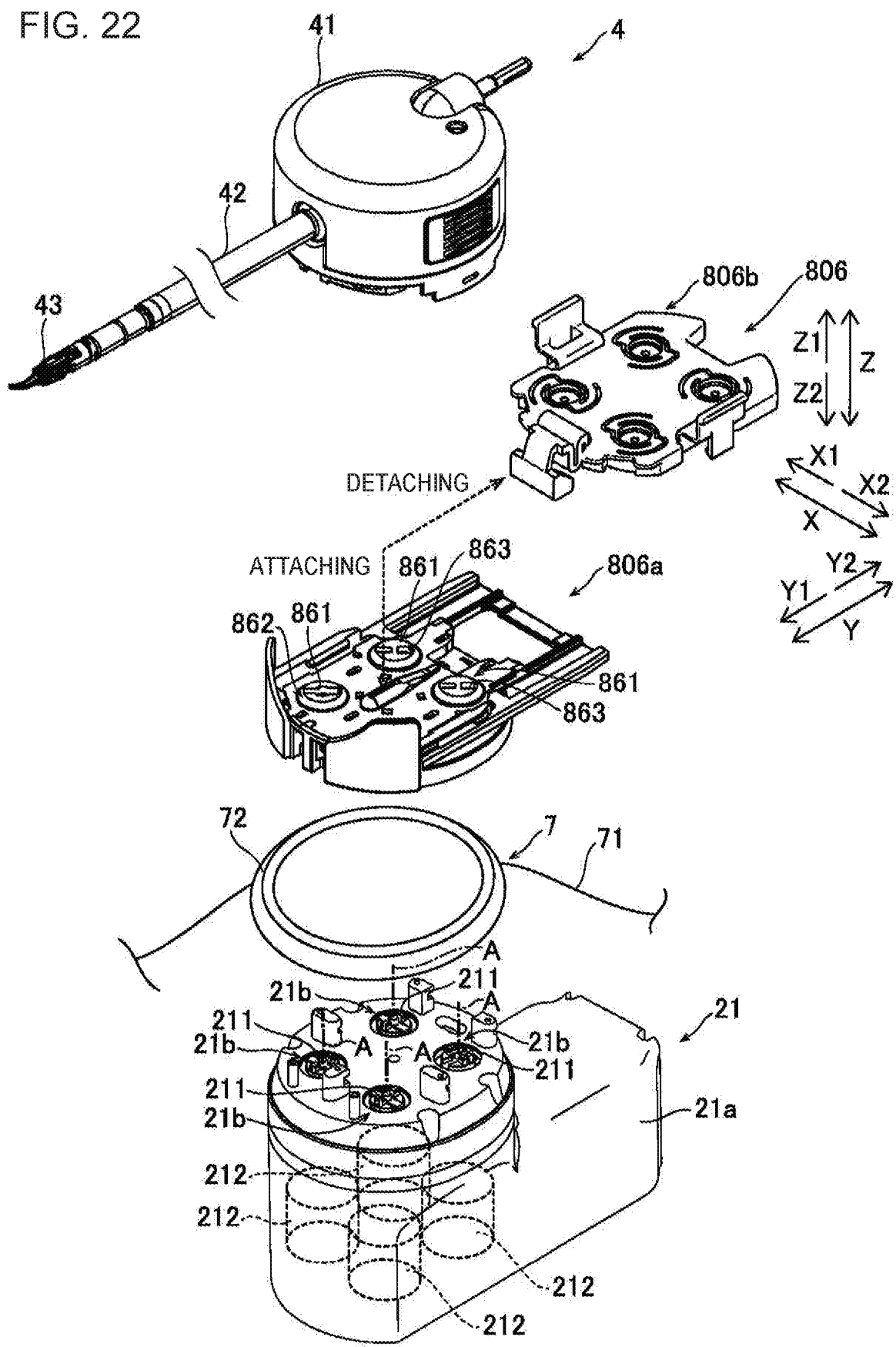
FIG. 22 is a diagram illustrating an exploded perspective view of a state where a surgical instrument is to be attached to a robot arm via an adaptor according to a second embodiment.
Figure 23:
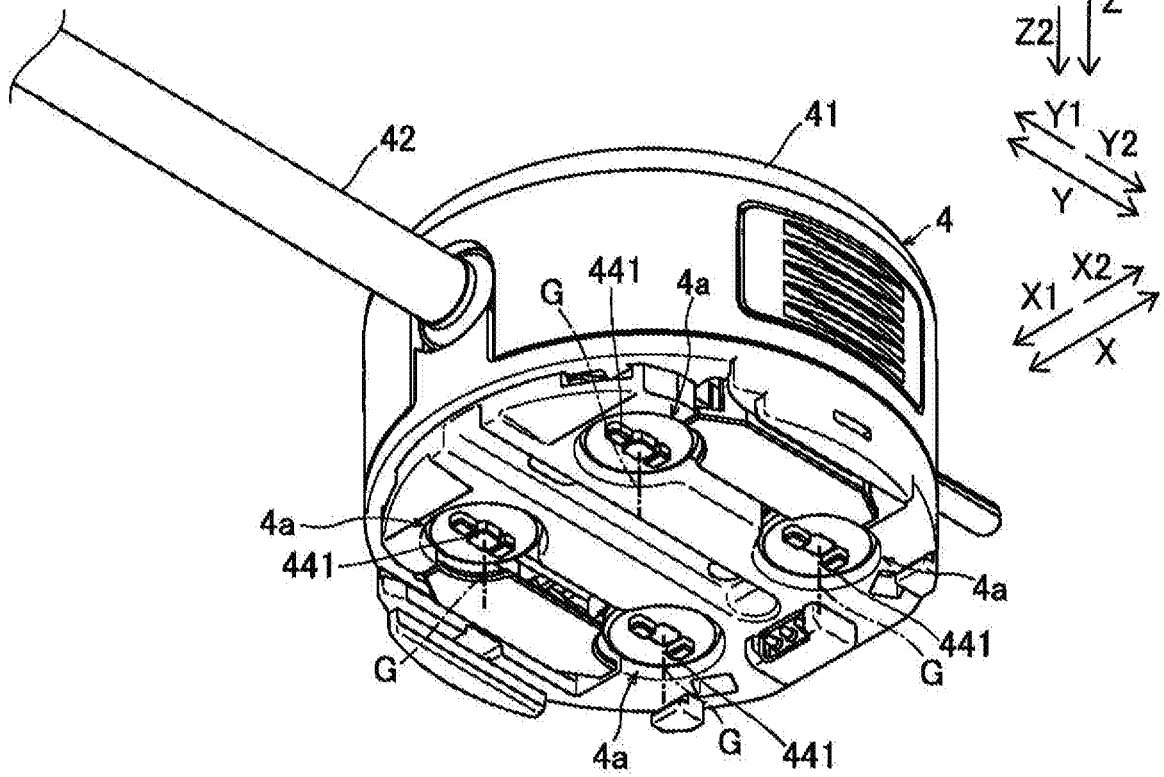
FIG. 23 is a diagram illustrating a perspective view of the surgical instrument according to a second embodiment.

As illustrated in FIGS. 22 and 23, in order to transmits the driving forces from the robot arm 21 to the end effector 43, each of the driven members 4a includes the engagement projection 441 to be engaged with the drive transmission members 861 of the adaptor main body 806a. The engagement projection 441 is projected from the Z2 side surface of the driven member 4a toward the side of the adaptor main body 806a (the Z2 side). The engagement projection 441 includes plural projected portions linearly arranged.

Figure 24:
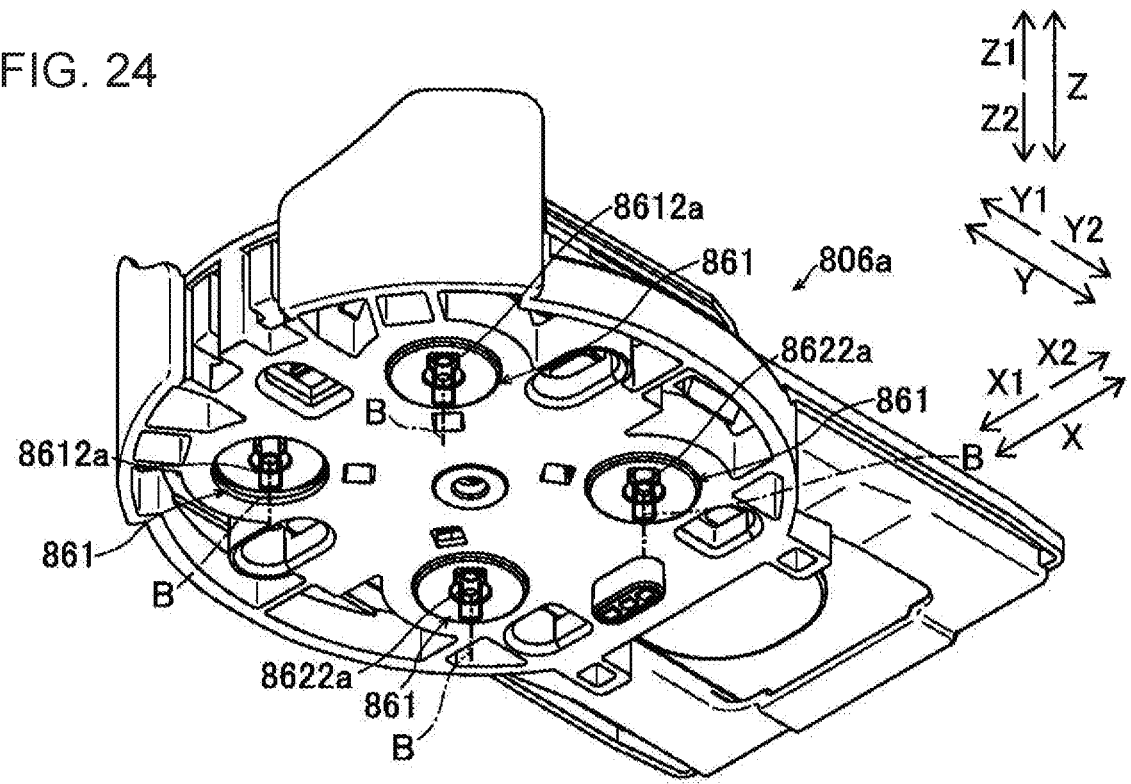
FIG. 24 is a diagram illustrating a perspective view of an adaptor main body according to a second embodiment as viewed from the Z2 side.
Figure 25:
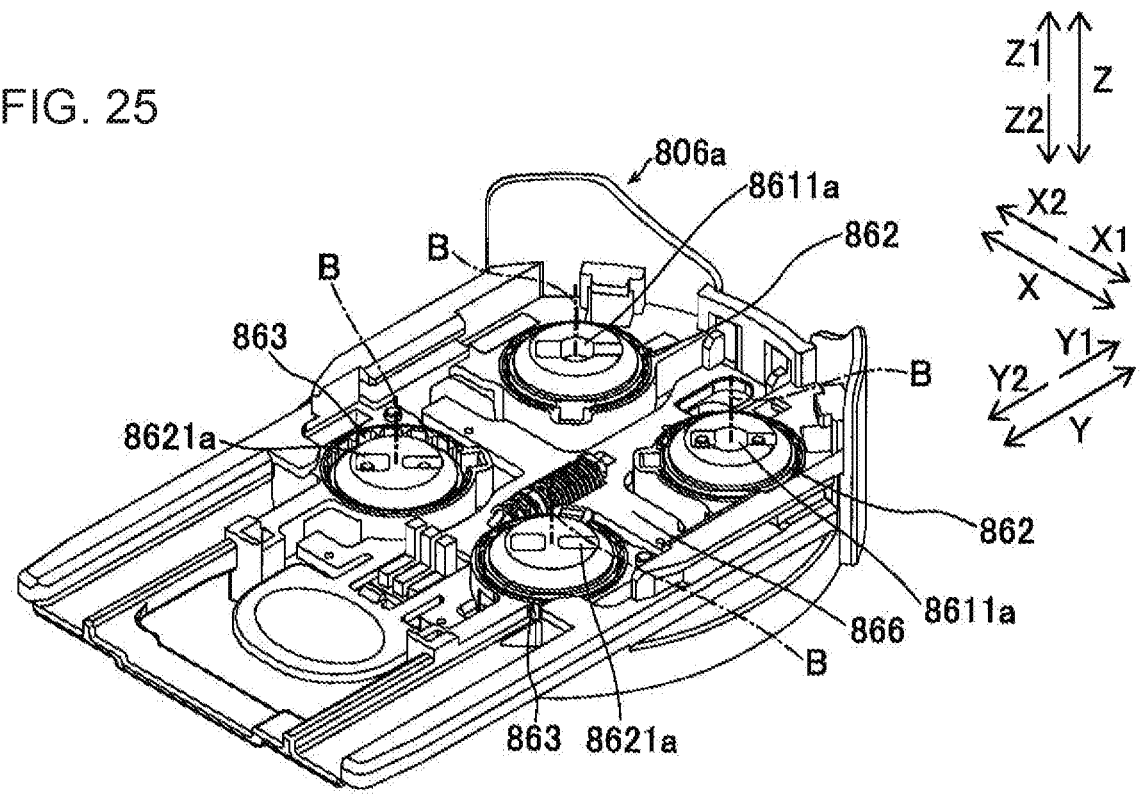
FIG. 25 is a diagram illustrating a perspective view of the adaptor main body according to a second embodiment as viewed from the Z1 side.

As illustrated in FIGS. 24 and 25, the adaptor main body 806a includes a plurality (four) of the drive transmission members 861. Among the four drive transmission members 861, two of the drive transmission members 861 provided on the Y1 side (hereinafter, referred to as first drive transmission members 862) has the same shape. Among the four drive transmission members 861, the other two of the drive transmission members 861 provided on the Y2 side (hereinafter, referred to as second drive transmission members 863) has the same shape. Note that in FIG. 25, the stopper 806b, which is to cover the upper side of the adaptor main body 806a, is detached from the adaptor main body 806a.

Figure 26:
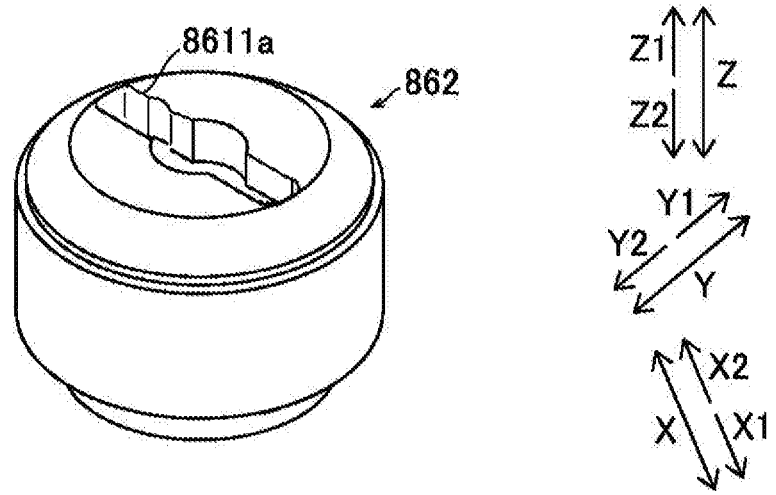
FIG. 26 is a diagram illustrating a perspective view of a first drive transmission member of the adaptor main body according to a second embodiment.
Figure 27:
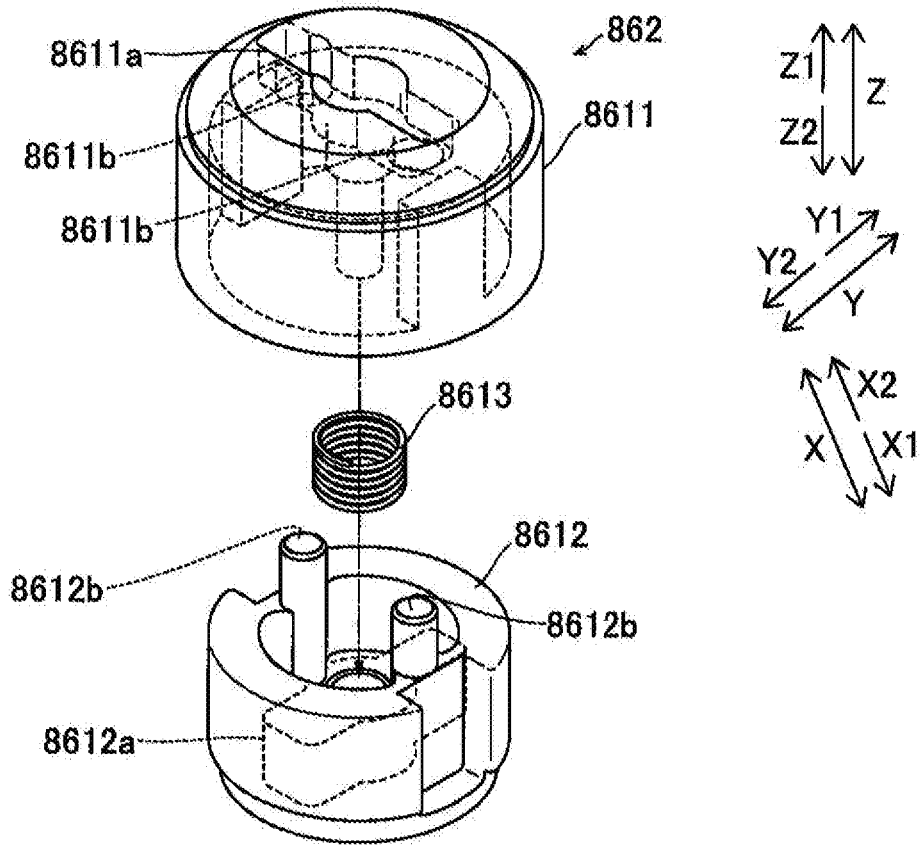
FIG. 27 is a diagram illustrating an exploded perspective view of the first drive transmission member of the adaptor main body according to a second embodiment.

First, with reference to FIGS. 26 and 27, the first drive transmission members 862 provided on the Y1 side are described below. Since the two first drive transmission members 862 on the Y1 side have the same shape, only one of the first drive transmission members 862 provided on the X1 side is described below to avoid redundancy.

The first drive transmission member 862 includes a first member 8611, a second member 8612, and a spring 8613. Each of the first member 8611 and the second member 8612 has a substantially circular cylindrical shape. The first member 8611 is provided on the Z1 side with respect to the second member 8612 and the second member 8612 is provided on the Z2 side with respect to the first member 8611. The spring 8613 is a compression spring (a compression coil spring). The spring 8613 is accommodated in the second member 8612. The spring 8613 biases the first member 8611 toward the Z1 side and biases the second member 8612 toward the Z2 side.

The first member 8611 includes an engagement recess 8611*a* and through holes 8611*b*.

The engagement recess 8611*a* is formed as a recess extending in the direction orthogonal to the direction of the rotational axis B (see FIG. 24). The engagement recess 8611*a* is to be engaged with the engagement projection 441 of the corresponding driven member 4*a* of the surgical instrument 4. The engagement recess 8611*a* is provided on a surface of the drive transmission member 861 on the surgical instrument 4 side (the Z1 side). The engagement recess 8611*a* is recessed from the Z1 side surface of the drive transmission member 861 toward the direction (the Z2 side) away from the surgical instrument 4. Each of the through holes 8611*b* penetrates through a portion of the first member 8611 where the engagement recess 8611*a* is provided. The through holes 8611*b* are formed corresponding to later-described projections 8612*b*.

The second member 8612 includes an engagement recess 8612*a* and the projections 8612*b*.

The engagement recess 8612*a* is formed as a recess extending in the direction orthogonal to the direction of the rotational axis B (See FIG. 24). The engagement recess 8612*a* is to be engaged with the engagement projection 211 of the corresponding drive part 21*b* of the robot arm 21. The engagement recess 8612*a* is provided at a portion of the drive transmission member 861 on the robot arm 21 side (the Z2 side). The engagement recess 8612*a* is recessed from the Z2 side surface of the drive transmission member 861 toward the direction (the Z1 side) away from the robot arm 21. The engagement recess 8612*a* and the engagement recess 8611*a* are arranged orthogonal to each other as viewed along the Z direction. Each of the projections 8612*b* extends in the direction of the rotational axis B of the drive transmission member 861. The projections 8612*b* of the second member are inserted in the through holes 8611*b* of the first member 8611.

Figure 28:
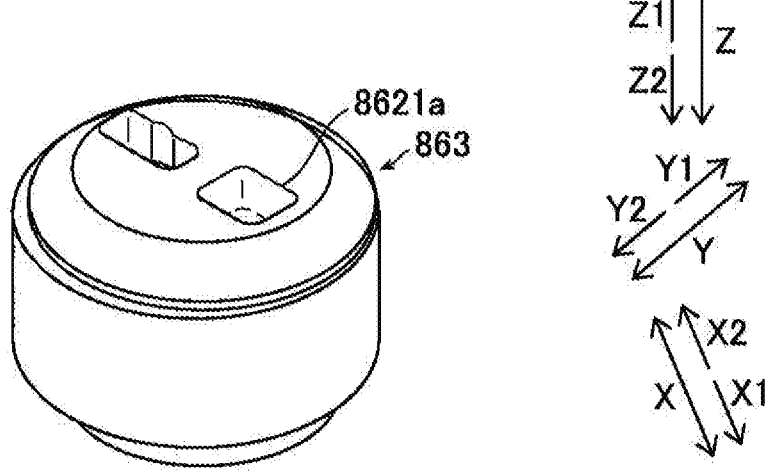
FIG. 28 is a diagram illustrating a perspective view of a second drive transmission member of the adaptor main body according to a second embodiment.
Figure 29:
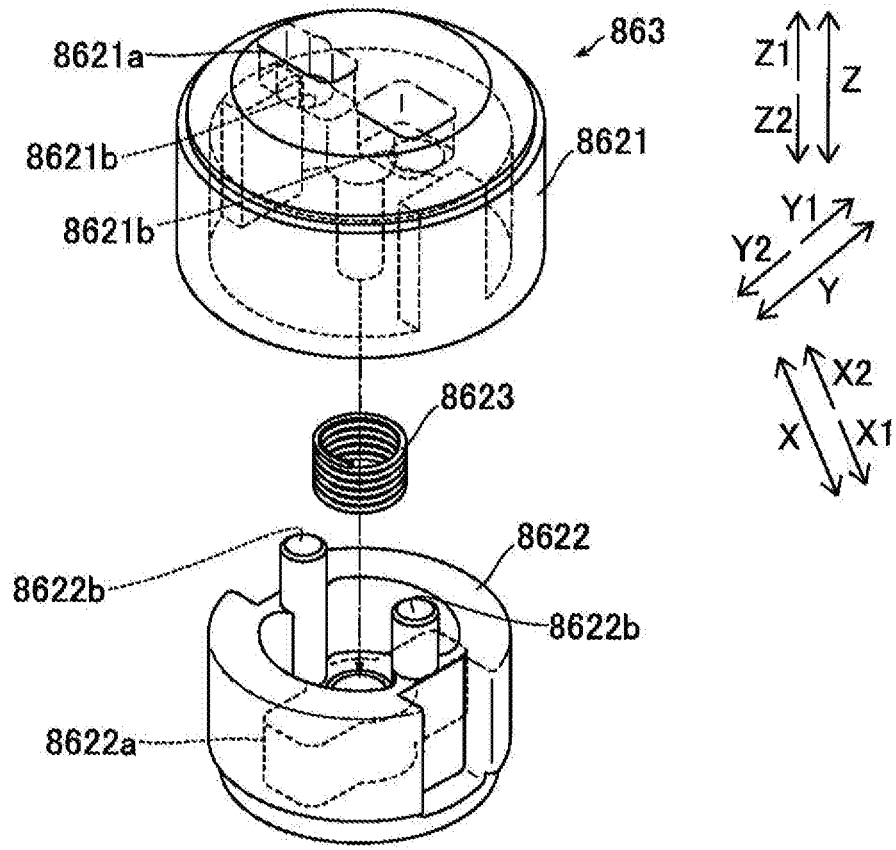
FIG. 29 is a diagram illustrating an exploded perspective view of the second drive transmission member of the adaptor main body according to a second embodiment.

With reference to FIGS. 28 and 29, the second drive transmission members 863 provided on the Y2 side are described below. Since the two second drive transmission members 863 on the Y2 side have the same shape, only one of the second drive transmission members 863 provided on the X1 side is described below to avoid redundancy.

The second drive transmission member 863 includes a first member 8621, a second member 8622, and a spring 8623. The first member 8621 includes an engagement recess 8621*a* and through holes 8621*b*. The second member 8622 includes an engagement recess 8622*a* and projections 8622*b*. Note that the second drive transmission member 863 has the same configuration as the first drive transmission member 862 except of that of the engagement recesses, and thus description for the configuration other than the engagement recesses is omitted below to avoid redundancy.

Figure 30:
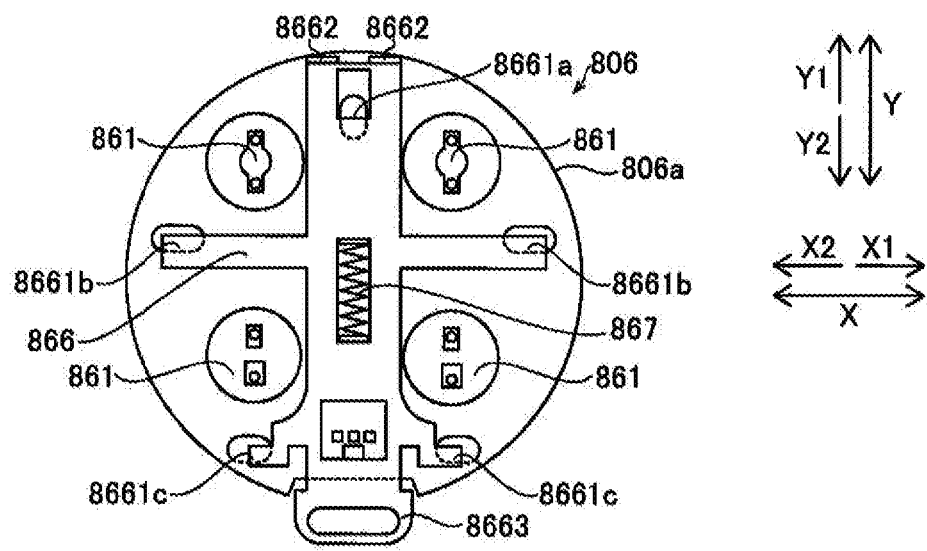
FIG. 30 is a diagram illustrating a plan view of an engagement state of an arm engagement portion of the adaptor main body according to a second embodiment.
Figure 31:
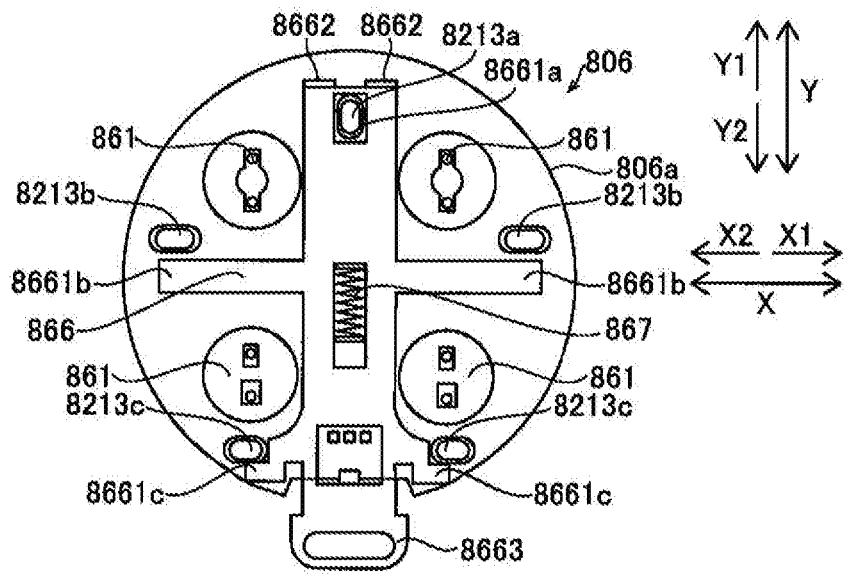
FIG. 31 is a diagram illustrating a plan view of a released state of the arm engagement portion of the adaptor main body according to a second embodiment.

The engagement recess 8621*a* includes two recess portions arranged side by side in the direction orthogonal to the direction of the rotational axis B (FIG. 24). The engagement recess 8621*a* and the engagement recess 8622*a* are arranged orthogonal to each other as viewed along the Z direction The adaptor 806 includes an arm engagement portion 866 as illustrated in FIGS. 30 and 31. The arm engagement part 866 is provided in the adaptor main body 806*a*. The arm engagement part 866 is disposed in the adaptor main body 806*a* to be slidable in the Y direction. The arm engagement part 866 includes an engagement portion 8661*a*, an engagement portion 8661*b*, an engagement portion 8661*c*, a restriction portion 8662, and an operation portion 8663. The engagement portion 8661*a*, the engagement portion 8661*b*, the engagement portion 8661*c*, the restriction portion 8662, and the operation portion 8663 of the arm engagement part 866 are integrally formed. The arm engagement part 866 is biased toward the Y1 side by a bias member 867. Note that the arm engagement part 866 is an example of an engagement portion for the drive part.

The engagement portion 8661*a* is provided at a portion of the arm engagement part 866 on the Y1 side. The engagement portion 8661*c* is provided at an end portion of the arm engagement part 866 on the Y2 side. The engagement portion 8661*b* is provided between the engagement portion 8661*a* and the engagement portion 8661*c* in the Y direction.

In the state where the surgical instrument 4 is attached to the adaptor main body 806*a*, the restriction portion 8662 is in contact with the surgical instrument 4 to restrict movements of the arm engagement part 866.

Specifically, the restriction portion 8662 is provided to be protruded toward the surgical instrument 4 side. The operation portion 8663 is provided for moving the arm engagement part 866 in the Y2 direction against the biasing force of the bias member 867. The operation portion 8663 is operated by the worker to be pulled toward the Y2 side.

Figure 32:
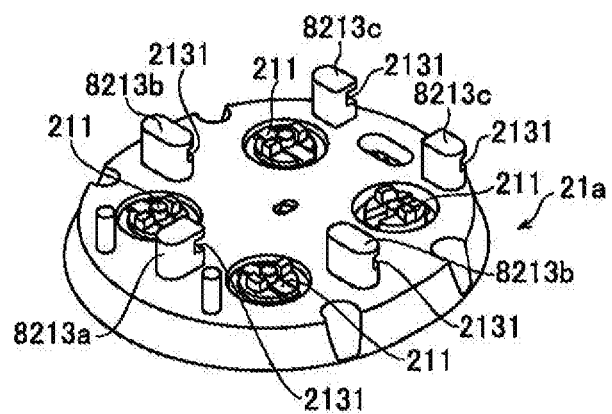
FIG. 32 is a diagram illustrating a perspective view illustrating a Z1 side portion of the drive part according to a second embodiment.

As illustrated in FIG. 32, the robot arm 21 includes the frame 21*a* and the plural (four) drive parts 21*b* (see FIG. 8). Each of the drive parts 21*b* includes the engagement projection 211 and the actuator 212 (see FIG. 8). The robot arm 21 includes an engagement projection 8213*a*, an engagement projection 8213*b*, and an engagement projection 8213*c*.

The engagement projections 211 of the drive parts 21*b* are engaged with the engagement recesses 8612*a* and the engagement recesses 8622*a* of the drive transmission members 861. Each of the engagement projections 211 is projected from the Z1 side surface of the drive part 21*b* toward the Z1 side (the adaptor main body 806*a* side). Each of the engagement projections 211 has a line-symmetric shape. The actuator 212 includes the motor. The actuator 212 is configured to drive the engagement projection 211 to rotate about the rotational axis A extending in the Z direction.

The engagement projection 8213*b* includes plural (two) engagement projections 8213*b* and the engagement projection 8213*c* includes plural (two) engagement projections 8213*c*.

The engagement projection 8213*a*, the engagement projections 8213*b*, and the engagement projections 8213*c* of the robot arm 21 are configured to be engaged with the adaptor 806. Specifically, each of the engagement projection 8213*a*, the engagement projections 8213*b*, and the engagement projections 8213*c* includes a groove 2131 opened toward the Y2 side. To the grooves 2131 of the engagement projection

8213*a*, the engagement projections 8213*b*, and the engagement projections 8213*c* of the robot arm 21, the engagement portion 8661*a*, the engagement portions 8661*b*, and the engagement portions 8661*c* of the arm engagement part 866 of the adaptor 806 are to be engaged.

When the arm engagement part 866 is moved to the Y1 side, the engagement portions 8661*a*, 8661*b*, and 8661*c* are engaged with the engagement projections 8213*a*, 8213*b*, and 8213*c*. With this operation, the robot arm 21 and the adaptor 806 are engaged with each other. On the other hand, when the arm engagement part 866 is moved to the Y2 side, the engagement of the engagement portions 8661*a*, 8661*b*, and 8661*c* with the engagement projections 8213*a*, 8213*b*, and 8213*c* is released. With this operation, the engagement between the robot arm 21 and the adaptor 806 is released.

(Configuration of Stopper)

Figure 33:
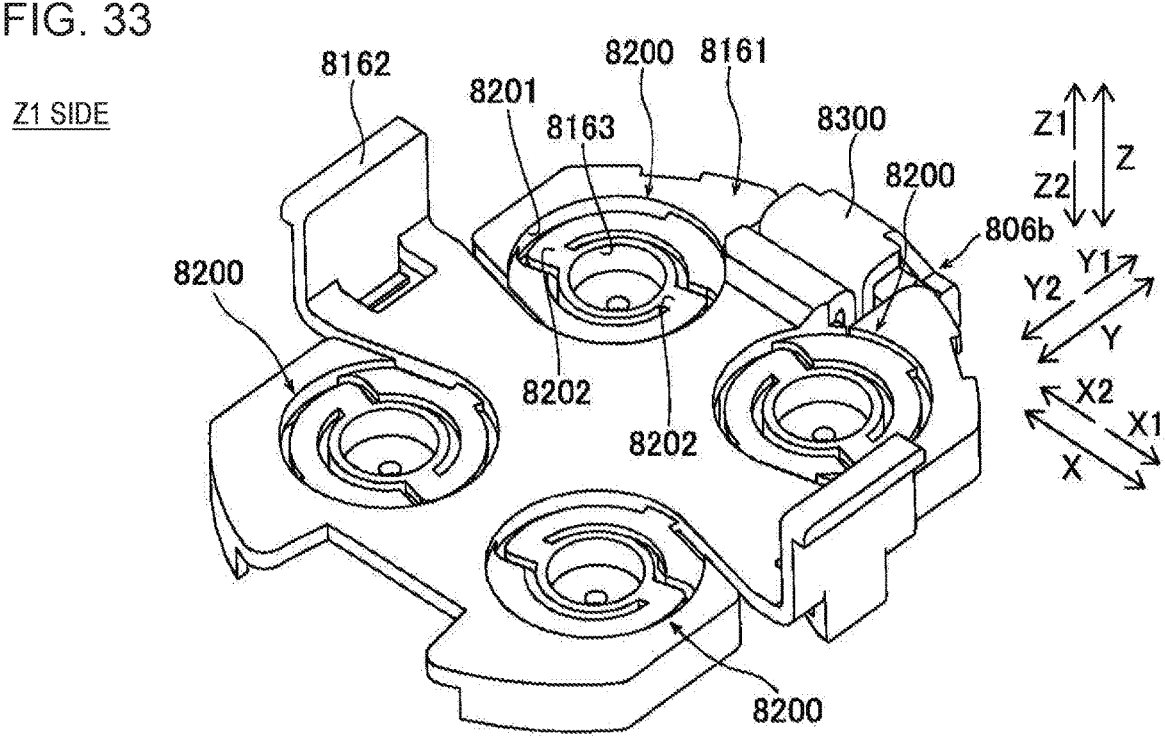
FIG. 33 is a diagram illustrating a perspective view of a stopper according to a second embodiment as viewed from the Z1 side.
Figure 34:
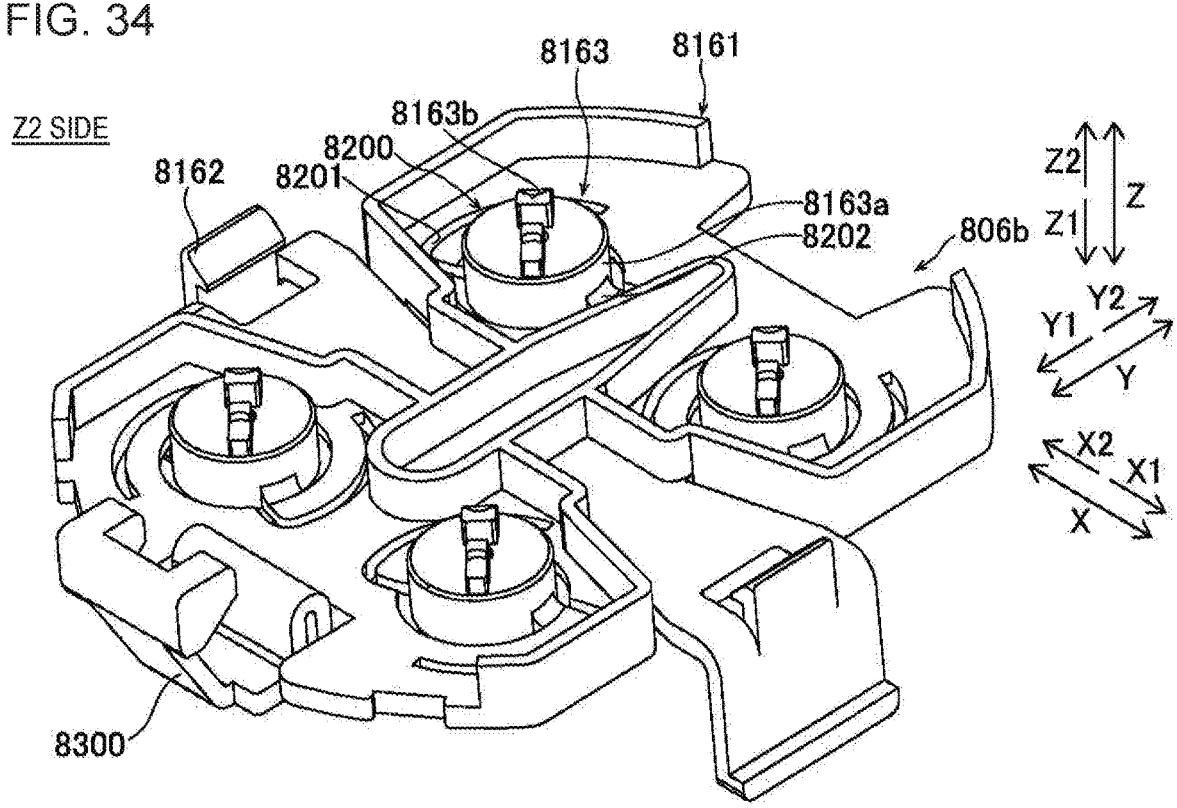
FIG. 34 is a diagram illustrating a perspective view of the stopper according to a second embodiment as viewed from the Z2 side.

As illustrated in FIGS. 33 and 34, the adaptor 806 includes the stopper 806*b* which is attached to the adaptor main body 806*a*. The stopper 806*b* according to a second embodiment is configured to have portions, corresponding to the drive transmission members 861 of the adaptor main body 806*a*, which can be independently deformed when the stopper 806*b* is attached to the adaptor main body 806*a*.

Specifically, the stopper 806*b* includes a stopper body 8161, an attachment portion 8162, and the rotation restriction portion 8163. The configuration of the attachment portion 8162 of the stopper 806*b* is the same as that of the stopper 6*b* according to a first embodiment, and thus the description thereof is omitted to avoid redundancy.

(Rotation Restriction Portion)

Each of the rotation restriction portions 8163 is configured, when the stopper 806*b* is attached to the adaptor main body 806*a*, to be movable in the direction of the rotational axis B (see FIG. 24) of the drive transmission members 861 of the adaptor main body 806*a*.

With this, when the stopper 806*b* is attached to the adaptor main body 806*a*, each of the rotation restriction portions 8163 comes in contact with the corresponding drive transmission member 861, and thus can be moved in the direction away from the drive transmission member 861, to prevent an excessive load from being applied to the drive transmission member 861. Therefore, until later-described fitting projections 8163*b* of the rotation restriction portions 8163 are fitted to the engagement recesses 8611*a* or the engagement recesses 8621*a* of the drive transmission members 861, the drive transmission members 861 can be smoothly rotated.

The plural rotation restriction portions 8163 are provided corresponding to the plural drive transmission members 861 provided in the adaptor main body 806*a*. The plural rotation restriction portions 8163 are independently movable in the direction of the rotational axis B of the drive transmission members 861 of the adaptor main body 806*a*.

With this configuration, even when any one of the plural drive transmission members 861 is fitted to the corresponding one of the plural rotation restriction portions 8163, the other rotation restriction portions 8163, which are not yet fitted, can be independently moved in the direction of the rotational axis B and thus can be prevented from being over-pressed by the corresponding drive transmission members 861. Therefore, it is possible that the rotations of the drive transmission members 861, corresponding to the other rotation restriction portions 8163 which are not yet fitted, are not prevented.

Each rotation restriction portion 8163 is resiliently movable in the direction (Z direction) of the rotational axis B (see FIG. 24) of the drive transmission member 861 of the adaptor main body 806*a* by means of a later-described support beam 8202. Note that the plural (four) rotation restriction portions 8163 are provided in the stopper body 8161 and all of them have the same shape, and thus one of the plural rotation restriction portions 8163 is described below to avoid redundancy.

Figure 35:
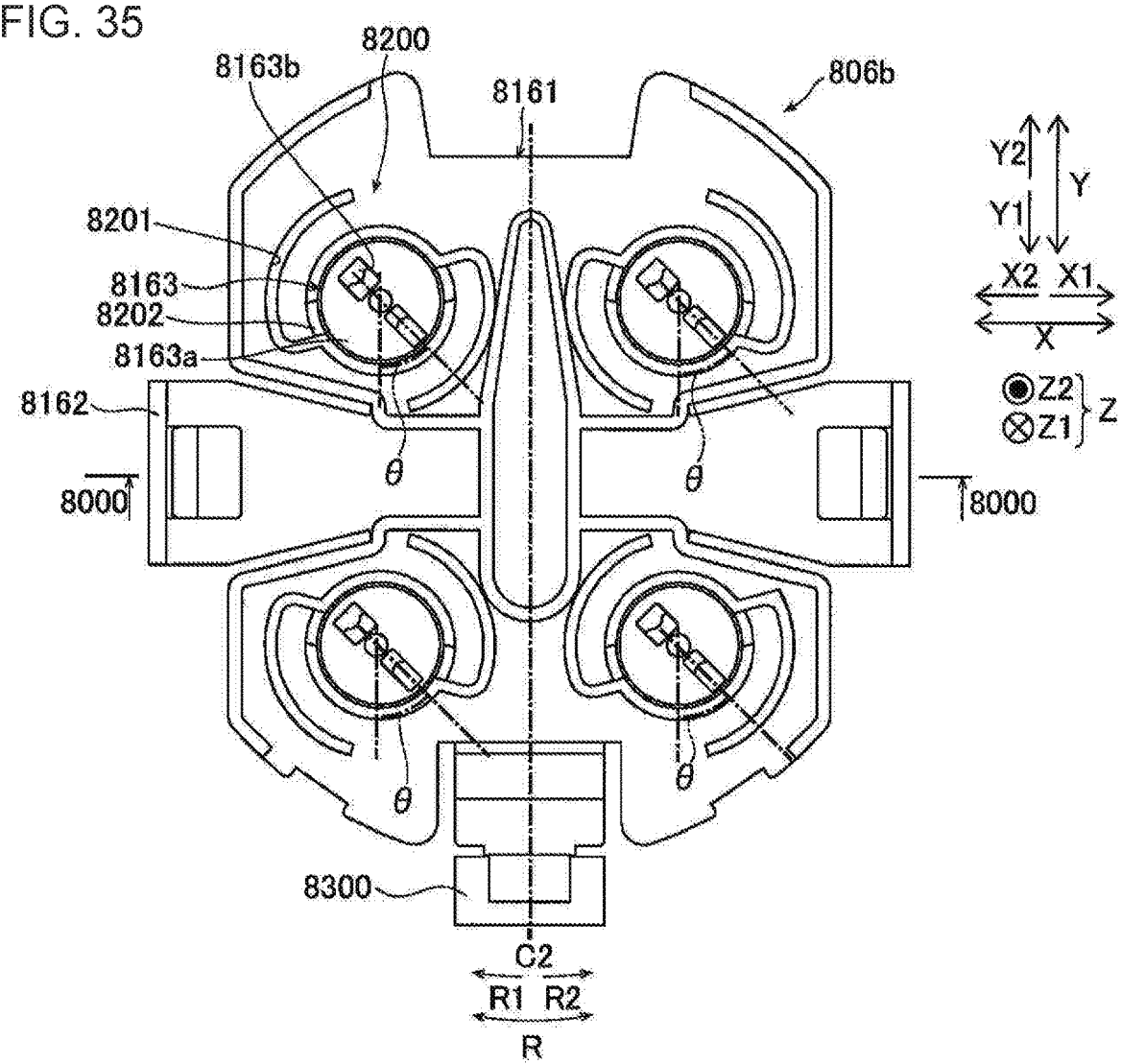
FIG. 35 is a diagram illustrating a plan view of the stopper according to a second embodiment as viewed from the Z2 side.

As illustrated in FIGS. 34 and 35, the rotation restriction portion 8163 includes a base portion 8163*a* and the fitting projection 8163*b*. The base portion 8163*a* has a substantially circular cylindrical shape. The base portion 8163*a* of the rotation restriction portion is provided at a position to be in contact with the Z1 side surface of the corresponding drive transmission member 861 of the adaptor main body 806*a*. The diameter of the base portion 8163*a* of the rotation restriction portion corresponds to the diameter of the Z1 side surface of the drive transmission member 861 of the adaptor main body 806*a*, in the direction orthogonal to the Z direction. The base portion 8163*a* has a convex shape protruding from the stopper body 8161 toward the Z2 side. Note that the shape of the base portion 8163*a* is not limited to the convex shape protruding from the stopper body 8161 toward the Z2 side, and may be a concave shape recessed toward the Z1 side.

The fitting projection 8163*b* is provided to be inclined at the predetermined angle θ in the circumferential direction R with respect to the center axis C2 of the stopper body 8161 parallel to the longitudinal direction (Y direction) of the surgical instrument 4. The fitting projection 8163*b* is provided on the Z2 side surface of the base portion 8163*a* of each of the rotation restriction portions 8163. All of the plural (four) fitting projections 8163*b* are inclined at the same predetermined angle θ with respect to the center axis C2 of the stopper body 8161. Specifically, all of the plural fitting projections 8163*b* are inclined at the same predetermined angle θ from the center axis C2 of the stopper body 8161 toward the second circumferential direction R2. Note that the fitting projections 8163*b* may be inclined at the predetermined angle θ from the center axis C2 toward the first circumferential direction R1.

Since all of the plural fitting projections 8163*b* have the same structure, one of the fitting projections 8163*b* is described below to avoid redundancy.

The fitting projection 8163*b* of the stopper 806*b* is in contact with an inner surface of the engagement recess 8611*a* or the engagement recess 8621*a* of the corresponding drive transmission member 861 of the adaptor main body 806*a*, and thus restricts the rotation of the drive transmission member 861 with being inclined by the predetermined angle θ with respect to the center axis C2 toward the second circumferential direction R2.

Specifically, the fitting projection 8163*b* is configured to be fit into the engagement recess 8611*a* or the engagement recess 8621*a* of the adaptor main body 806*a*. The fitting projection 8163*b* is provided on the Z2 side surface of the base portion 8163*a* with being inclined at the predetermined angle θ.

Figure 36:
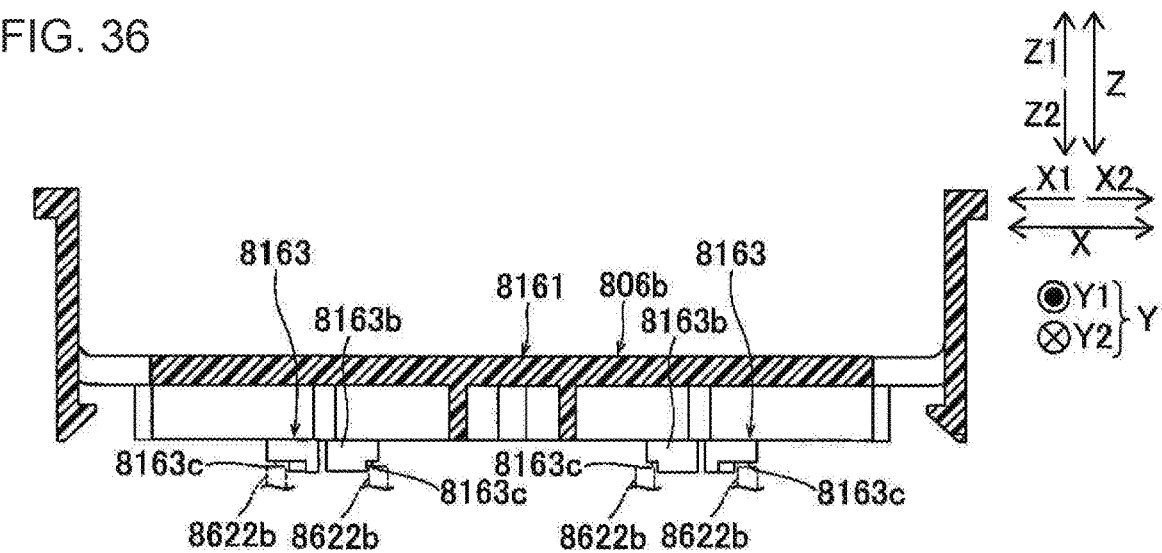
FIG. 36 is a diagram illustrating a sectional view taken along line 8000-8000 in FIG. 35.

As illustrated in FIGS. 35 and 36, the fitting projection 8163*b* has a block shape (substantially rectangular parallelepiped shape). The fitting projection 8163*b* is projected from the Z2 side surface of the base portion 8163*a* toward the Z2 side. The fitting projection 8163*b* has divided two pieces arranged in the direction inclined at the predetermined angle θ with respect to the center axis C2. The fitting projection 8163*b* is formed with an escape portion 8163*c* (or a clearance portion). The escape portion 8163*c* is formed to make a clearance from or to escape from the projection 8612*b* or 8622*b* of the drive transmission member 861. The escape portion 8163*c* have a cutout shape or a recessed shape on the fitting projection 8163b. The escape portion 8163c is formed to be aligned with the projection 8612b or 8622b of the corresponding drive transmission member 861. The escape portion 8163c is formed at each of end portions of the fitting projection 8163b in the direction inclined at the predetermined angle θ with respect to the center axis C2.
(Resiliently Deformable Portion)

The stopper body 8161 includes resiliently deformable portions 8200 which can be resiliently deformed to move the rotation restriction portions 8163 in the direction of the rotational axis B of the drive transmission members 861 of the adaptor main body 806a when the stopper body 8161 is attached to the adaptor main body 806a.

With this, by only resiliently deforming the resiliently deformable portions 8200, the rotation restriction portions 8163 are moved in the direction of the rotational axis B of the drive transmission members 861 of the adaptor main body 806a. Therefore, the stopper 806b can have a simple structure.

Figure 37:
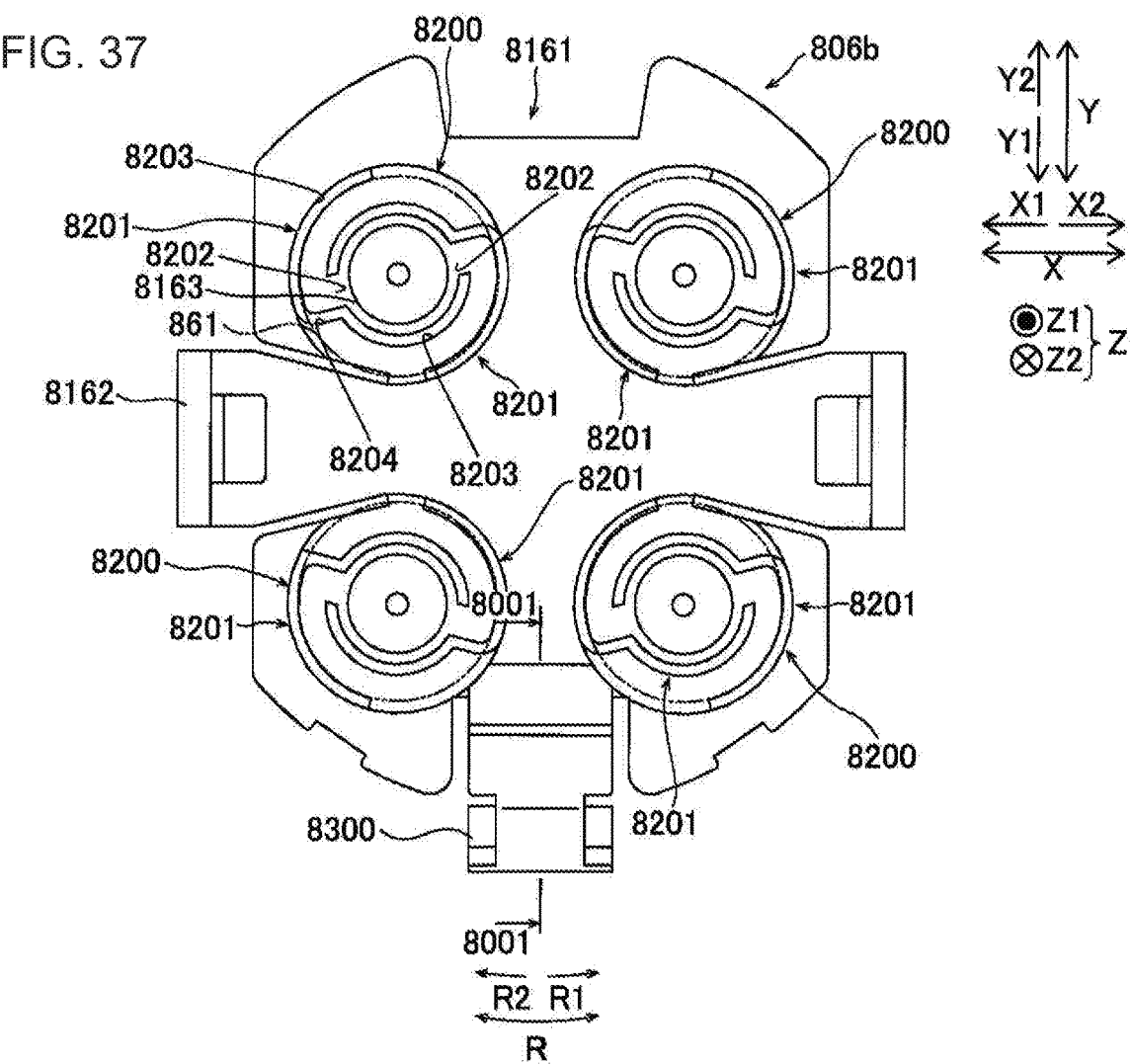
FIG. 37 is a diagram illustrating a plan view of the stopper according to a second embodiment as viewed from the Z1 side.

As illustrated in FIGS. 33 and 37, each of the resiliently deformable portions 8200 is formed by making the stiffness property of a portion around the base portion 8163a in the stopper body 8161 lower than the stiffness properties of the other portions. Specifically, the resiliently deformable portion 8200 is formed to have the stiffness property of the portion around the base portion 8163a in the stopper body 8161, such that the stiffness property thereof against the load along the Z direction is lower than the stiffness property thereof against the load along the circumferential direction R.

The resiliently deformable portion 8200 includes a slit(s) 8201 and the support beam 8202. The slit 8201 is formed around the rotation restriction portion 8163 of the stopper body 8161. The support beam 8202 is defined by the slit 8201 of the stopper body 8161 and resiliently supports the rotation restriction portion 8163 to be movable in the direction of the rotational axis B of the drive transmission member 861 of the adaptor main body 806a.

The stiffness of the portion around the rotation restriction portion 8163 is decreased by means of the slit 8201, the resiliently deformable portion 8200 can thus be more easily bent than other portions of the stopper body 8161. In addition, the amount of stroke of the rotation restriction portion 8163 when the resiliently deformable portion 8200 bends can be ensured by the length of the support beam 8202. Therefore, by means of the slit 8201 and the support beam 8202, the rotation restriction portion 8163 can be moved in the direction of the rotational axis B of the drive transmission member 861 of the adaptor main body 806a by a desired stroke amount.
(Slit)

As illustrated in FIG. 37, the slit 8201 penetrates in the Z direction through the portion of the stopper body 8161 around the base portion 8163a. Specifically, the slit 8201 has a plurality (two) of arc-shaped portions 8203 having different lengths and connecting portions 8204 connecting the plurality of the arc-shaped portions 8203 to each other. The arc-shaped portions 8203 extend along the circumferential direction R. The connecting portions 8204 extend along the direction orthogonal to the Z direction. Note that the slit 8201 may not have the connecting portions 8204.

A plurality (eight) of the slits 8201 are formed in the stopper body 8161. A plurality (two) of the slits 8201 are formed around each base portion 8163a so as to surround each base portion 8163a. The slits 8201 are formed at positions corresponding to the drive transmission members 861 of the adaptor main body 806a. In the direction orthogonal to the Z direction, the size of the slit 8201 matches the size of the drive transmission member 861 of the adaptor main body 806a. That is, in the direction orthogonal to the Z direction, the position of the outer circumference of the slit 8201 is located outside the position of the outer circumference of the Z2 side surface of the drive transmission member 861 of the adaptor main body 806a.
(Support Beam)

As illustrated in FIG. 33, the support beam 8202 is formed as a double-supported beam. That is, the support beam 8202 supports an end of the rotation restriction portion 8163 in the X1 direction and an end of the rotation restriction portion 8163 in the X2 direction. Further, the support beam 8202 has a function of an elastic (resilient) member, such as a resin spring. Specifically, the support beam 8202 is configured to enable the rotation restriction portion 8163 to move in the Z direction and to suppress the movement of the rotation restriction portion 8163 in the circumferential direction R. The support beam 8202 is configured to secure the stroke amount of the rotation restriction portion 8163 in the Z direction. Specifically, the support beam 8202 has an arc shape extending long in the circumferential direction R.

Accordingly, upon the operation of attaching the stopper 806b to the adaptor main body 806a, when the drive transmission member 861 of the adaptor main body 806a comes in contact with the fitting projection 8163b before the fitting projection 8163b is completely fit into the engagement recess 8611a or 8621a, the support beam 8202 allows the rotation restriction portion 8163 to move in the Z1 direction. The support beam 8202 also allows the base portion 8163a in the Z2 direction when the fitting projection 8163b is fit in the engagement recess 8611a or 8621a of the adaptor main body 806a.
(Press Portion)

Figure 38:
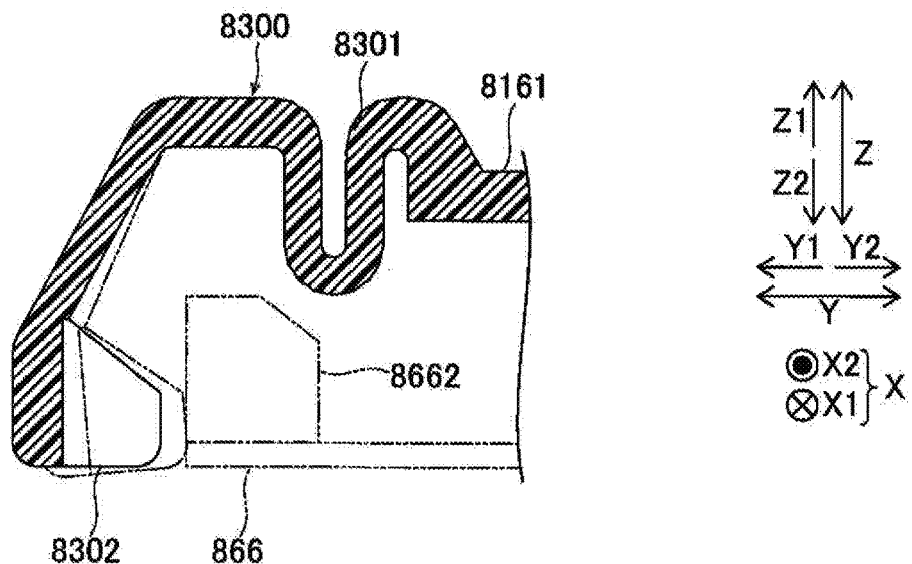
FIG. 38 is a diagram illustrating a sectional view taken along line 8001-8001 in FIG. 37.

As illustrated in FIGS. 37 and 38, the stopper body 8161 includes a press portion 8300. The press portion 8300 is pressed to move the arm engagement part 866 that engages the drive part 21b with the adaptor main body 806a in the direction (the Y2 direction) that releases the engagement between the drive part 21b and the adaptor main body 806a in the state where the stopper body 8161 is attached to the adaptor main body 806a.

With this configuration, when the worker presses the press portion 8300 in the state where the stopper 806b is attached to the adaptor main body 806a (indicated by a two-dot chain line in FIG. 38), the arm engagement part 866 can be moved toward the Y2 side. That is, the worker can attach the adaptor main body 806a to the drive parts 21b of the robot arm 21 without pulling the operation portion 8663. Therefore, the adaptor main body 806a can be easily attached to the drive parts 21b of the robot arm 21. In addition, in the state where the stopper 806b is attached to the adaptor main body 806a, the engagement between the adaptor main body 806a and the drive parts 21b can be released without the worker pulling the operation portion 8663.

The press portion 8300 is configured to press the restriction portion 8662 of the arm engagement part 866 in the Y2 direction in the state where the stopper 806b is attached to the adaptor main body 806a. The press portion 8300 is integrally formed with a portion of the stopper body 8161 on the Y1 side, Specifically, the press portion 8300 includes a spring portion 8301 and a contact portion 8302. The spring portion 8301 connects the stopper body 8161 and the contact portion 8302. The contact portion 8302 is protruded from a portion of the spring portion 8301 on the Z2 side toward the Y2 side. The contact portion 8302 has a tapered shape that becomes thinner toward the Y2 side.

(Method of Assembling Adaptor)

Figure 39:
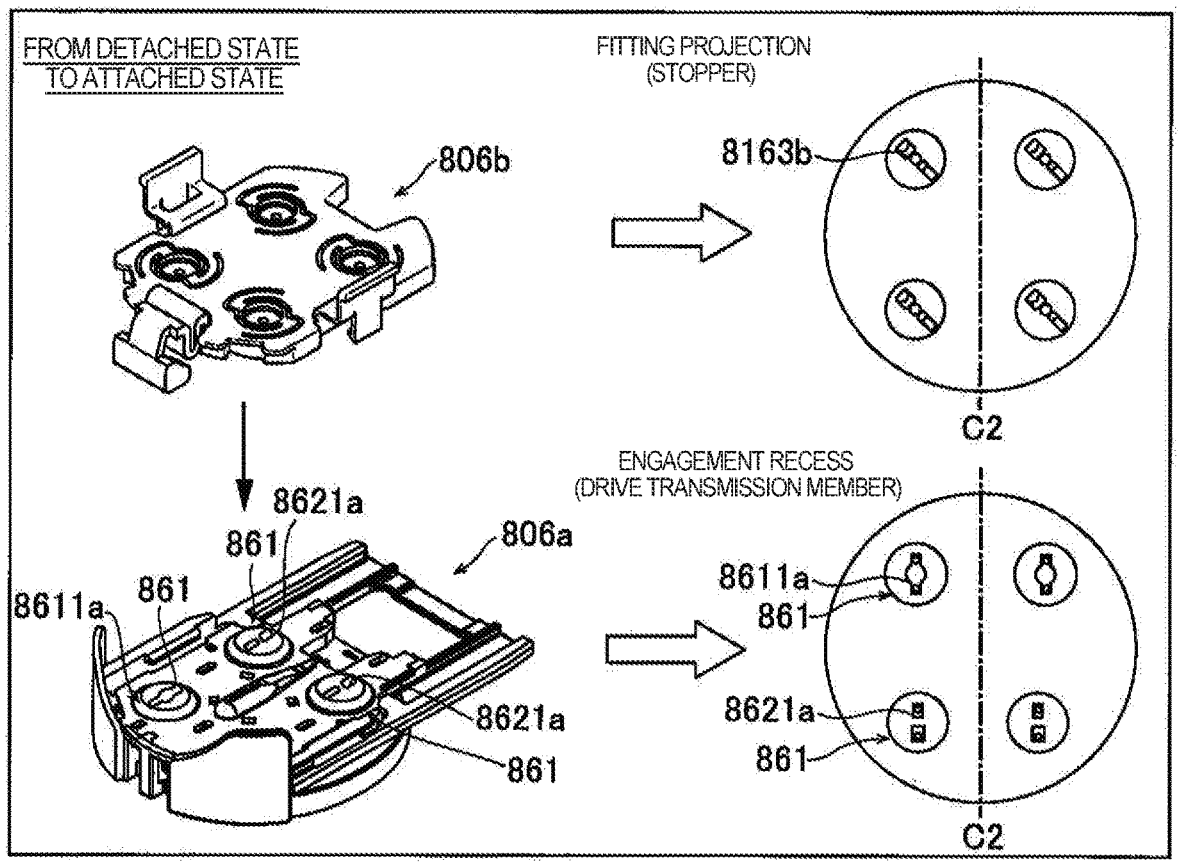
FIG. 39 is a diagram illustrating a schematic view of a state when the stopper is attached to the drive transmission members according to a second embodiment.
Figure 40:
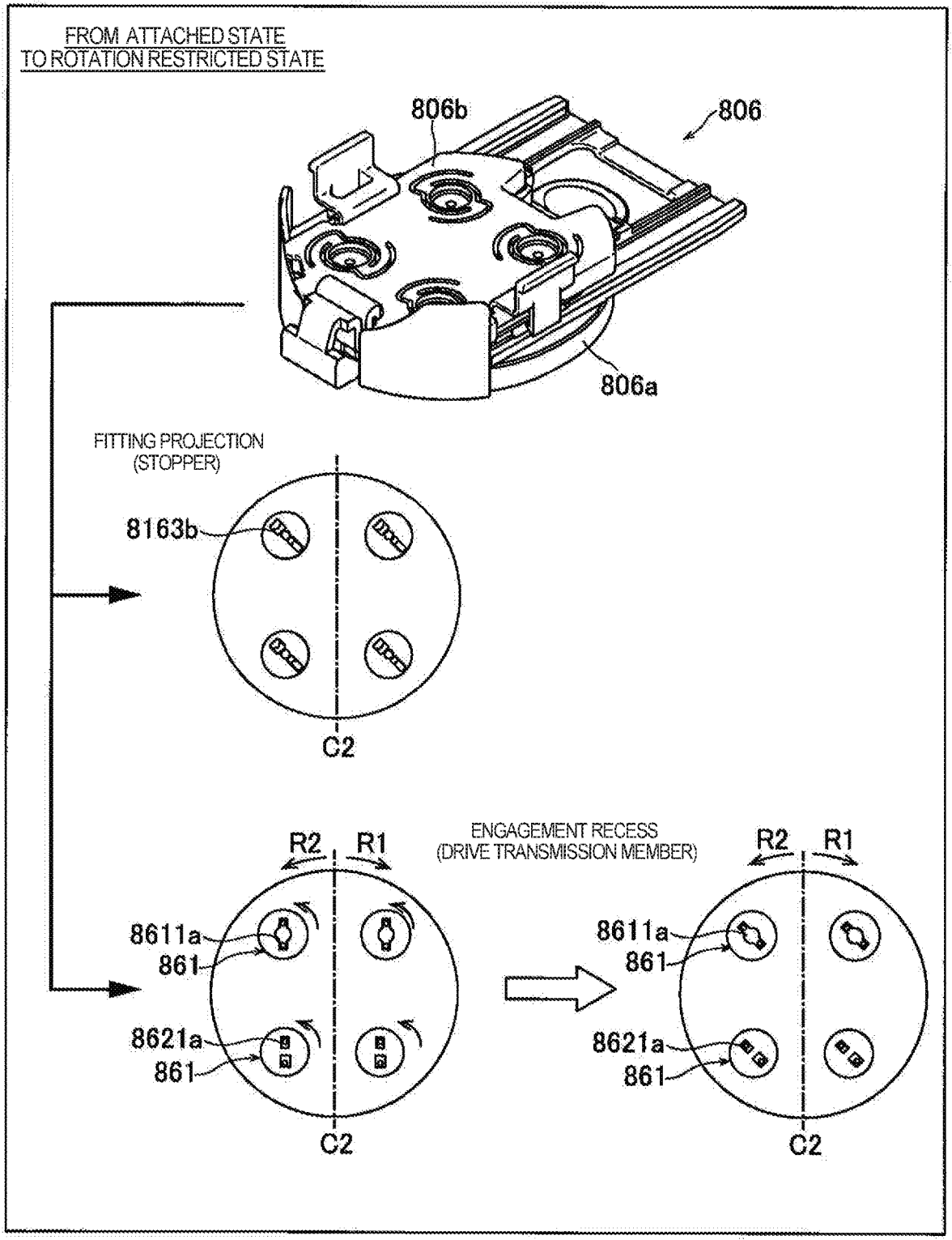
FIG. 40 is a diagram illustrating a schematic view of a state in which rotations of the drive transmission members are restricted by the stopper according to a second embodiment.

With reference to FIGS. 15, 39, and 40, a method of assembling the adaptor 806 including the adaptor main body 806a and the stopper 806b is described below. With this assembling method, the adaptor 806 in which the positions of the engagement recesses 8611a and 8621a of the adaptor main body 806a are fixed and held at the predetermined angle θ. Note that in FIGS. 39 and 40, the center axis C2 is illustrated on the adaptor main body 806a to facilitate understanding. In addition, the first circumferential direction R1 and the second circumferential direction R2 are also illustrated on the adaptor main body 806a to facilitate understanding.

As illustrated in FIG. 15, in Step S1, the worker assembles the adaptor main body 806a.

In Step S2, the worker attaches the stopper 806b to the adaptor main body 806a. That is, as illustrated in FIG. 39, the worker puts the stopper 806b closer to the adaptor main body 806a and attaches the stopper 806b to the adaptor main body 806a in the state the fitting projections 8163b of the stopper 806b are in contact with the drive transmission members 861 of the adaptor main body 806a. As a result, the pair of the attachment portion 8162 of the stopper 806b and the pair of the guide rails of the adaptor main body 806a are respectively engaged with each other. In this state, the fitting projections 8163b of the stopper 806b are inclined with the direction of the center axis C2 by the predetermined angle θ, while the engagement recesses 8611a and 8621a of the adaptor main body 806a are substantially parallel to the direction of the center axis C2.

As illustrated in FIG. 15, in Step S3, the worker rotates the drive transmission members 861 of the adaptor main body 806a to thereby fitting the engagement recesses 8611a and 8621a of the adaptor main body 806a and the fitting projections 8163b of the stopper 806b to each other. Specifically, as illustrated in FIG. 40, the worker rotates the drive transmission members 861 of the adaptor main body 806a manually (for example, operating directly by hand or using a tool) in the state where the stopper 806b is attached to the adaptor main body 806a, to thereby fit the engagement recesses 8611a and 8621a of the adaptor main body 806a and the fitting projections 8163b of the stopper 806b to each other. At this time the worker rotates the engagement recesses 8611a and the engagement recess 8621a of the adaptor main body 806a in the second circumferential direction R2.

With this operation, the adaptor 6 in the rotation restricted state where the rotational positions (rotational angles) of the engagement recesses 8611a and 8621a of the adaptor main body 806a are fixed and held at the predetermined angle θ is assembled. Then, the operation of assembling the adaptor 6 by the worker is ended.

(Modifications)

The one or more embodiments disclosed above are meant to be illustrative in all respects and should not be construed to be limiting in any manner. The scope of the invention is defined not by the above-described one or more embodiments, but by the scope of claims, and includes all modifications (variations) within equivalent meaning and scope to those of the claims.

Figure 41:
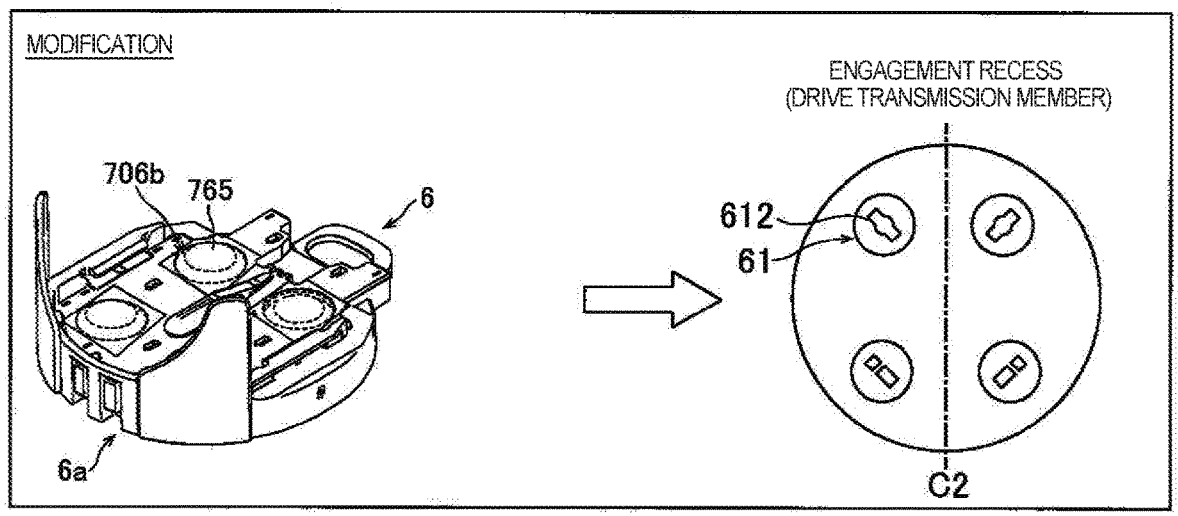
FIG. 41 is a diagram illustrating a schematic view of a stopper according to a modification of first and second embodiments.

For example, in above described first and second embodiments, the adaptor 6 (806) includes the stopper 6b (806b) to fix the rotational positions of the engagement recesses 611 (8611a, 8621a) of the adaptor main body 6a (806a) to the predetermined inclined angle θ. However, the disclosure is not limited to this. For example, in a modification as illustrated in FIG. 41, a stopper 706b may have tapes 765 to fix the rotational positions of the engagement recesses 611 of the adaptor main body 6a to the predetermined inclined angle θ. In this case, an adhesive layer of the tape 765 forms a rotation restriction portion, and a base body of the tape 765 on which the adhesive layer is provided forms a stopper body.

In above described first and second embodiments, the robot arm 21 includes the lamp 21d whose lighting state is changed when the engagement between the robot arm 21 and the adaptor main body 6a (806a) is completed and when the engagement between the adaptor main body 6a and the surgical instrument 4 is completed. However, the disclosure is not limited to this. For example, in a modification, a robot arm may include a notification part such as a sound generator to generate sound when an engagement between the robot arm and an adaptor main body is completed and/or when the engagement between the adaptor main body and a surgical instrument is completed.

In above described first and second embodiments, the attachment portion 664 (8162) is configured to attach the stopper body 64 (8161) to the adaptor main body 6a (806a) when the stopper body 64 (8161) is put closer to the adaptor main body 6a (806a) in the Z direction and to detach the stopper body from the adaptor main body when the stopper body is put away from the adaptor main body in the Z direction. However, the disclosure is not limited to this. For example, in a modification, an attachment portion may be configured to attach a stopper body to an adaptor main body when the stopper body is slid closer to the adaptor main body in the Y direction and to detach the stopper body from the adaptor main body when the stopper body is slid away from the adaptor main body in the Y direction.

In above described first and second embodiments, the plural (four) fitting projections 665 (8163b) are provided on the surface of the stopper body 64 (8161) opposed to the surgical instrument 4 side surface 63 of the adaptor main body 6a (806a). However, the disclosure is not limited to this. For example, in a modification, the number of fitting projections may be set corresponding to the number of drive transmission recesses of an adaptor main body, and may be one to three or more than four.

In above described first embodiment, the plural fitting projections 665 are arranged on the stopper body 64 to be line-symmetric with respect to the center axis C2 of the stopper body 64 and be inclined at the predetermined angle θ with respect to the center axis C2. However, the disclosure is not limited to this. For example, in a modification, plural fitting projections may be provided to be aligned with drive transmission recesses of an adaptor main body, but the plural fitting projections are not required to be line-symmetrically arranged with respect to a center axis of a stopper body like a second embodiment.

In above described first and second embodiments, the number of the plural fitting projections 665 (8163b) provided on the X1 side with respect to the center axis C2 of the stopper body 64 (8161) and the number of the plural fitting projections 665 (8163b) provided on the X2 side with respect to the center axis C2 of the stopper body 64 (8161) are the same. However, the disclosure is not limited to this. For example, in a modification, the number of plural fitting projections provided on a X1 side with respect to a center axis of a stopper body and the number of the plural fitting projections provided on a X2 side with respect to the center axis of the stopper body may be different. Also, plural fitting projections may be provided on only the X1 side or the X2 side with respect to a center axis of a stopper body.

In above described first and second embodiments, the discrimination portion 667 includes the first discrimination portion 667a in which one side portion of the stopper body 64 (8161) is smaller than the other side portion of the stopper body in the Y direction and the second discrimination portion 667b having the recess or the cutout at only one side of the rim of the stopper body 64 in the longitudinal direction of the surgical instrument. However, the disclosure is not limited to this. For example, in a modification, a discrimination portion may include only one of a first discrimination portion in which one side portion of a stopper body is smaller than the other side portion of the stopper body in a longitudinal direction of a surgical instrument and a second discrimination portion having a recess or a cutout at only one side of a rim of the stopper body. In this case, the discrimination portion provided at the stopper body have a simple structure, and this can further prevent a complicated and enlarged structure of the stopper body.

In above described first and second embodiments, the encoder 215 detects the drive states of the drive parts 21b. However, the disclosure is not limited to this. For example, in a modification, a controller may detect a drive states of drive parts by measuring electrical current value(s) applied to motor(s) of the drive part(s).

In above described first and second embodiments, the stopper 6b (806b) is provided with the fitting projections 665 (8163b), and the adaptor main body 6a (806a) is provided with the engagement recesses 611 (8611a, 8621a). However, the disclosure is not limited to this. For example, in a modification, a stopper may be provided with a fitting recess(es) and an adaptor main body may be provided with a fitting projection(s).

In above described first and second embodiments, the adaptor main body 6a (806a) and the drape 7 are separated from each other. However, the disclosure is not limited to this. For example, in a modification, the adaptor main body 6a (806a) and the drape 7 may be integrally formed with each other.

The invention claimed is:

1. A stopper to be attached to an adaptor main body, wherein the adaptor main body is to be provided between a drive part provided at a robot arm and a surgical instrument and the adaptor main body includes a drive transmission member to transmit a driving force from the drive part to the surgical instrument, comprising:
    a stopper body; and
    a rotation restriction portion provided at the stopper body and configured to restrict rotations of the drive transmission member, wherein
    the stopper is configured such that the rotation restriction portion restricts the rotations of the drive transmission member in a state where the stopper body is attached to the adaptor main body and the rotation restriction portion releases the restriction of the rotations of the drive transmission member in a state where the stopper body is detached from the adaptor main body.

2. The stopper according to claim 1, wherein
the stopper body includes an attachment portion to detachably attach the stopper body to the adaptor main body.

3. The stopper according to claim 2, wherein
the attachment portion includes a pair of engagement portions to be detachably engaged with the adaptor main body and to restrict movements of the stopper body with respect to the adaptor main body.

4. The stopper according to claim 3, wherein
the pair of engagement portions is detachably engaged with a pair of guide rails, wherein the pair of guide rails is provided at the adaptor main body and configured to guide attachment of the surgical instrument to the adaptor main body.

5. The stopper according to claim 3, wherein
the attachment portion includes a pair of grab portions to resiliently deform a part of the stopper body to move the pair of engagement portions in a direction away from the adaptor main body or in a direction toward the adaptor main body.

6. The stopper according to claim 1, wherein
the rotation restriction portion is inclined by a predetermined angle with respect to a center axis of the stopper body parallel to a longitudinal direction of the surgical instrument, in a circumferential direction about a rotational axis of the drive transmission member.

7. The stopper according to claim 6, wherein
the rotation restriction portion includes a fitting projection to be fit in a drive transmission recess, wherein the drive transmission recess is provided at the drive transmission member and recessed, toward a direction away from the surgical instrument, from a surface of the drive transmission member on a side of the surgical instrument, and
the fitting projection is formed at the stopper body with being inclined at the predetermined angle.

8. The stopper according to claim 7, wherein
the fitting projection includes a plurality of fitting projections.

9. The stopper according to claim 8, wherein
the plurality of fitting projections are line-symmetrically arranged with respect to the center axis of the stopper body parallel to the longitudinal direction of the surgical instrument.

10. The stopper according to claim 7, wherein
the rotation restriction portion includes a restriction portion recess provided around the fitting projection and recessed in a direction away from the adaptor main body, wherein the drive transmission member is to be inserted in the restriction portion recess.

11. The stopper according to claim 1, wherein
the stopper body includes a discrimination portion that indicates an orientation of the stopper with respect to a longitudinal direction of the surgical instrument upon attaching the stopper to the adaptor main body.

12. The stopper according to claim 11, wherein
the discrimination portion is configured to include at least one of a first discrimination portion in which one side portion of the stopper body is smaller than the other side portion of the stopper body in the longitudinal direction of the surgical instrument and a second discrimination portion including a recess at only one side, in the longitudinal direction of the surgical instrument, of an end of the stopper body.

13. The stopper according to claim 1, wherein
the rotation restriction portion is movable with respect to the stopper body in a direction of a rotational axis of the drive transmission member of the adaptor main body.

14. The stopper according to claim 13, wherein
the rotation restriction portion includes a plurality of rotation restriction portions provided corresponding to the drive transmission member including a plurality of drive transmission members provided at the adaptor main body, and the plurality of rotation restriction portions are independently movable with respect to the stopper body in the direction of the rotational axis of the drive transmission member of the adaptor main body.

15. The stopper according to claim 13, wherein
the stopper body includes a resiliently deformable portion to be resiliently deformed to move the rotation restriction portion in the direction of the rotational axis of the drive transmission member of the adaptor main body.

16. The stopper according to claim 15, wherein
the resiliently deformable portion includes: a slit formed at a portion of the stopper body around the rotation restriction portion; and a support beam supports the rotation restriction portion and is resiliently deformable to move the rotation restriction portion in the direction of the rotational axis of the drive transmission member of the adaptor main body.

17. The stopper according to claim 1, wherein
the stopper body includes a press portion configured, in a state where the stopper body is attached to the adaptor main body, to be pressed to move an engagement portion for the drive part that engages the drive part with the adaptor main body in a direction to release an engagement between the drive part and the adaptor main body.

18. A stopper to be attached to an adaptor main body, wherein the adaptor main body is to be provided between a drive part provided at a robot arm and a surgical instrument and the adaptor main body includes a drive transmission member to transmit a driving force from the drive part to the surgical instrument, comprising:
a stopper body;
a rotation restriction portion provided at the stopper body and configured to restrict rotations of the drive transmission member; and
an attachment portion provided at the stopper body and configured to detachably attach the stopper body to the adaptor main body, wherein
the rotation restriction portion restricts the rotations of the drive transmission member in a state where the stopper body is attached to the adaptor main body by the attachment portion.

19. Adaptor comprising:
an adaptor main body to be provided between a drive part provided at a robot arm and a surgical instrument and including a drive transmission member to transmit a driving force from the drive part to the surgical instrument; and
a stopper to be attached to the adaptor main body, wherein
the stopper includes:
a stopper body; and
a rotation restriction portion provided at the stopper body and configured to restrict rotations of the drive transmission member, wherein
the stopper is configured such that the rotation restriction portion restricts the rotations of the drive transmission member in a state where the stopper body is attached to the adaptor main body and the rotation restriction portion releases the restriction of the rotations of the drive transmission member in a state where the stopper body is detached from the adaptor main body.

20. The adaptor according to claim 19, wherein
the adaptor main body is configured such that a drape is attachable to the robot arm.

* * * * *